United States Patent
Allphin

(10) Patent No.: US 11,033,530 B2
(45) Date of Patent: Jun. 15, 2021

(54) DEVICES AND METHODS FOR FACILITATING AND CONTROLLING USE OF A MEDICATION

(71) Applicant: JAZZ PHARMACEUTICALS, INC., Palo Alto, CA (US)

(72) Inventor: Clark Allphin, Seattle, WA (US)

(73) Assignee: JAZZ PHARMACEUTICALS, INC., Palo Alto, CA (US)

( * ) Notice: Subject to any disclaimer, the term of this patent is extended or adjusted under 35 U.S.C. 154(b) by 0 days.

(21) Appl. No.: 15/714,456

(22) Filed: Sep. 25, 2017

(65) Prior Publication Data

US 2018/0147180 A1     May 31, 2018

Related U.S. Application Data

(63) Continuation of application No. 14/475,320, filed on Sep. 2, 2014, now Pat. No. 9,801,852.

(60) Provisional application No. 61/872,390, filed on Aug. 30, 2013.

(51) Int. Cl.

| A61K 31/365 | (2006.01) |
|---|---|
| A61K 31/19 | (2006.01) |
| A61K 31/191 | (2006.01) |
| A61J 3/00 | (2006.01) |
| A61K 31/485 | (2006.01) |
| A61K 31/22 | (2006.01) |
| A61J 7/00 | (2006.01) |

(52) U.S. Cl.
CPC ............... *A61K 31/365* (2013.01); *A61J 3/00* (2013.01); *A61J 7/0076* (2013.01); *A61K 31/19* (2013.01); *A61K 31/191* (2013.01); *A61K 31/22* (2013.01); *A61K 31/485* (2013.01); *A61J 3/002* (2013.01)

(58) Field of Classification Search
CPC .... A61J 7/0076; A61J 7/04; A61J 3/00; A61J 7/0427

See application file for complete search history.

(56) References Cited

U.S. PATENT DOCUMENTS

| 5,047,948 | A | 9/1991 | Turner |
|---|---|---|---|
| 9,061,879 | B2 | 6/2015 | Patthey |
| 9,801,852 | B2 | 10/2017 | Allphin |
| 2011/0034727 | A1 | 2/2011 | Luchi et al. |
| 2013/0068790 | A1* | 3/2013 | Patthey |
| 2015/0202588 | A1 | 7/2015 | Allphin |

OTHER PUBLICATIONS

Xyrem® FDA Approved Labeling Text, NDA 21-196/S-005, Nov. 18, 2005, 59 pages.*
Rhodium, "GHB (Gamma-Hydroxybutyrate) Synthesis FAQ", https://erowid.org/archive/rhodium/chemistry/ghb.html, Aug. 2004, downloaded on Sep. 10, 2016, pp. 1-9 of 9.

* cited by examiner

*Primary Examiner* — Savitha M Rao
*Assistant Examiner* — Gregg Polansky
(74) *Attorney, Agent, or Firm* — Cooley LLP

(57) ABSTRACT

A device includes a reservoir configured to store a drug formulation including at least one abuse-preventing additive. The device further includes means configured to remove the at least one abuse-preventing additive. The device further includes means configured to prevent access to the drug formulation.

19 Claims, 3 Drawing Sheets

DEVICES AND METHODS FOR FACILITATING AND CONTROLLING USE OF A MEDICATION

PRIORITY

This application is a continuation of U.S. Utility application Ser. No. 14/475,320 titled "DEVICES AND METHODS FOR FACILITATING AND CONTROLLING USE OF A MEDICATION", filed Sep. 2, 2014, and claims priority to U.S. Provisional Application 61/872,390 titled "METHOD FOR REDUCING OR PREVENTING ABUSE OR MISUSE OF A MEDICATION", filed Aug. 30, 2013, the disclosures of which are herein incorporated by reference in their entirety for all purposes.

FIELD OF THE INVENTION

Embodiments of the present invention are directed to a methods, devices, and formulations to facilitate proper use, deter accidental misuse and to reduce unauthorized use of medications, which can be controlled substances.

BACKGROUND OF THE INVENTION

Pharmaceutical products having abuse potential include narcotics, sedatives, stimulants and drugs from other categories. Of particular concern are narcotics, for which abuse-deterrent formulations have been developed using a variety of techniques. Most of these techniques aim to prevent alternative routes of administration for a prescribed drug, typically an oral product. The vast majority of such formulations have been solid dosage forms, and techniques have been developed to render such forms difficult to crush, extract using common household solvents, snort or inject due to physical characteristics. One common approach, for example, is to add an antagonist or other objectionable component that is sequestered from the beneficial drug, and remains sequestered in use unless the dosage form is manipulated, rendering the drug ineffective or undesirable. Examples of this include buprenorphine/naloxone combination (Suboxone, Reckitt Benckiser) and morphine/naltrexone (Embeda, King Pharmaceuticals); This basic approach, however, has severe limitations for some formulations such as liquids. For these, ion-exchange resins have been employed to limit release of the drug, inhibiting manipulation of the product to achieve a faster onset. An example of this is methylphenidate extended release (Quillivant XR, NextWave Pharma). For some drugs having very high therapeutic dose for a drug which require immediate release, such as sodium oxybate, use of resins is limited both by convenience of dosing a large amount of resin and also associated toxicological concerns.

There are other modes of abuse or misuse not addressed by existing methods of abuse deterrence. These are accidental misuse, intentional misuse for therapeutic benefit, surreptitious administration to others, and theft or diversion for unauthorized use. These are modes that do not necessarily apply to discrete dosage forms, such as tablets, pills, or capsules that can be counted and are difficult to take in partial increments, difficult to give to others accidentally or intentionally, and difficult to surreptitiously administer. For an oral solution, however, there are limited means of providing protection and assurance against any use other than prescribed.

Thus, there exists a need for providing devices, methods and formulations that protects against accidental use, diversion or misuse and also compliance to dosing instructions.

BRIEF SUMMARY OF THE INVENTION

In some embodiments, a method for preventing unauthorized use or abuse of a drug formulation comprises (a) providing a drug formulation comprising at least one of a drug, a prodrug, or precursor compound thereof, the formulation further comprising an abuse-preventing additive. The method further comprises (b) removing the abuse-preventing additive from the drug formulation of step (a) prior to administration, and (c) dispensing the drug formulation of step (b) to a patient in need thereof.

In some embodiments, a method for providing a drug comprises (a) providing an inactive form of a drug, and (b) chemically converting the inactive form of the drug in step (a) to an active form of the drug to provide a drug formulation usable by a patient in need thereof. The method further comprises (c) dispensing the drug formulation of step (b) to the patient in need thereof.

In some embodiments, a device comprises a reservoir configured to store a drug formulation including at least one abuse-preventing additive. The device further comprises means configured to remove the at least one abuse-preventing additive, and means configured to prevent access to the drug formulation.

In some embodiments, a drug formulation comprises a drug and at least one abuse-preventing additive that can be removed, or rendered harmless, prior to patient administration.

In some embodiments, a kit comprises a device, including a reservoir configured to contain a drug formulation including at least one abuse-preventing additive, wherein the abuse-preventing additive renders the drug formulation unpalatable. The device further includes means configured to remove the at least one abuse-preventing additive to render the drug formulation palatable, and means to prevent access to the drug formulation. The kit further comprises instructions for using the device.

In some embodiments, a method for preventing unauthorized use or abuse of a formulation of gamma hydroxybutyrate (GHB) comprises (a) providing GHB, or a prodrug or precursor compound thereof as a GHB formulation, the GHB formulation further comprising an abuse-preventing additive.

In some embodiments, a method for preventing unauthorized use or abuse of gamma hydroxybutyrate (GHB) comprises (a) providing an inactive form of GHB, (b) chemically converting the inactive form of GHB in step (a) to an active form of GHB, and (c) dispensing the active form of GHB of step (b) to a patient in need thereof.

In some embodiments, a gamma hydroxybutyrate (GHB) formulation comprises GHB, at least one or more of an aversive or a denaturing additive capable of being rendered ineffective prior to patient administration, and a pharmaceutically acceptable carrier. The GHB is present at a concentration of between 350 and 750 mg/mL in the GHB formulation, and the GHB formulation has a pH between 6.5 and 10.

In another embodiment, the invention includes a GHB composition that has been processed by a device to have substantially all of the abuse-preventing additive removed, altered or changed so that the composition is effective when administered to the patient and is also safe for human consumption and palatable. In another embodiment, the invention includes a GHB-containing dosage form, including a liquid dosage form, that has been processed by a device to have substantially all of the abuse-preventing additive removed, altered or changes to that the composition is effective when administered to the patient and is also safe for human consumption and palatable. In another embodiment, the processed GHB dosage form comprises a pharmaceutically acceptable carrier, the formulation containing GHB at a concentration of between 350 and 750 mg/mL and a pH between 6.5 and 10.

In some embodiments, a kit comprises a device, including a reservoir containing a gamma hydroxybutyrate (GHB) formulation including at least one abuse-preventing additive that renders the GHB formulation unpalatable, and means for removing the at least one abuse-preventing additive, wherein the GHB formulation is rendered palatable. The kit further comprises instructions for rendering the GHB formulation palatable using the device.

In some embodiments, a device comprises a product bag configured to hold a product including at least one abuse-preventing additive, and a treatment stack in fluid communication with the product bag, the treatment stack configured to receive the product and further configured to treat the product to render the abuse-preventing additive ineffective. The device further comprises a treatment reservoir configured to receive and store the treated product, and a dilution vessel coupled to the treatment reservoir, the dilution vessel configured to hold a single dose of the treated product. The device further comprises a dose receiver coupled to the dilution vessel, the dose receiver configured to dispense the single dose of the treated product.

In some embodiments, the device facilitates administration and control of GHB, the device optionally comprising: a reservoir to store a liquid drug formulation of gamma hydroxybutyrate, or a salt thereof; a reservoir for water or other diluent; piping and valves to fluidly connect the drug and the water reservoirs; a dosing platform comprising a balance to measure the amount of the drug dispensed into a cup or container; an alarm; a light; a clock; a locking mechanism; and software to control the operation of the device.

DETAILED DESCRIPTION OF THE INVENTION

Figure 1:
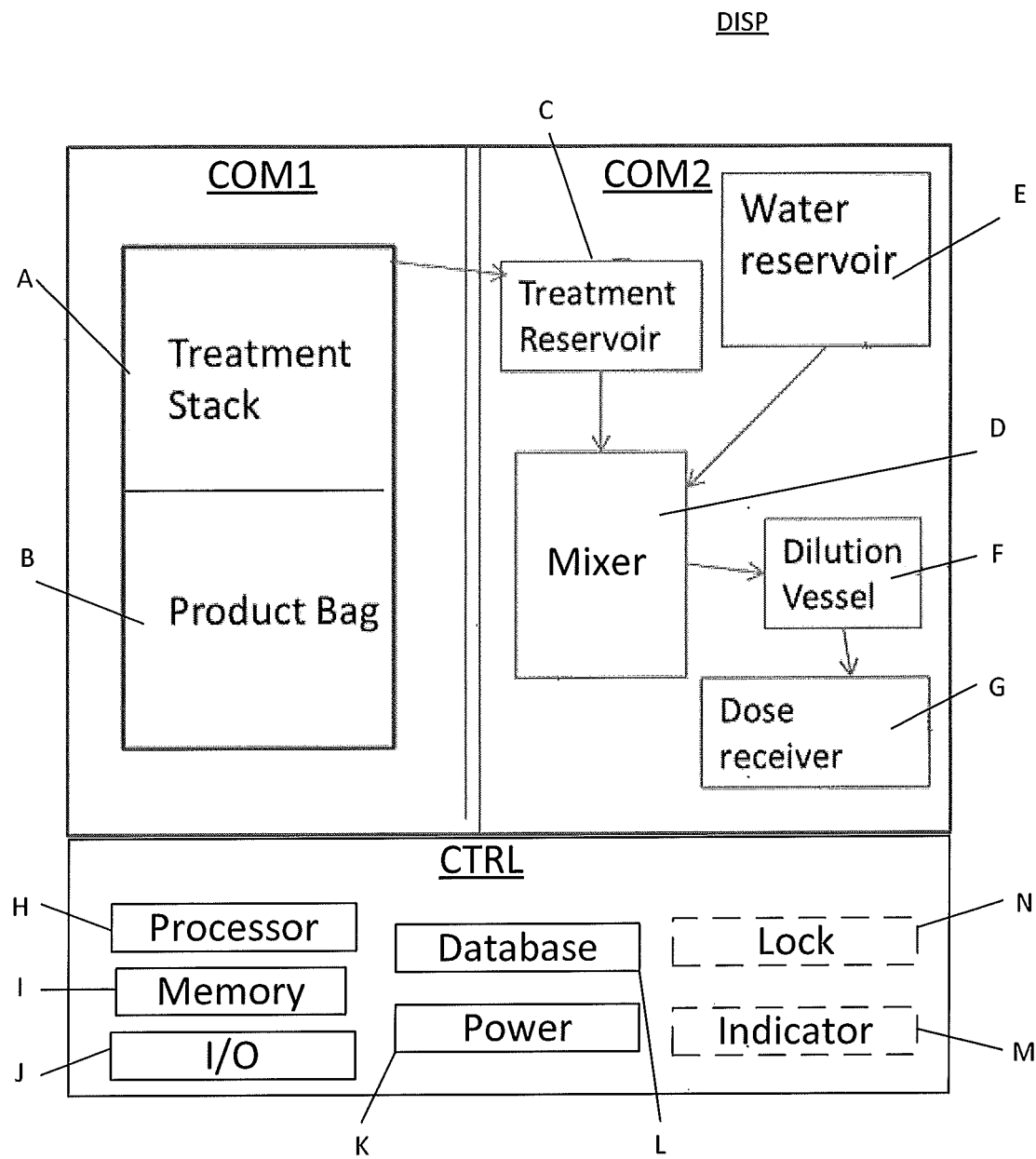
FIG. 1 illustrates a dispensing device, according to an embodiment.

One embodiment of the present invention relates to a device to facilitate secure, proper and convenient use of a controlled substance. In one embodiment of the present invention, adding one or more abuse-preventing agents to a controlled substance, such as sodium oxybate, commercially sold as Xyrem® by Jazz Pharmaceuticals. One embodiment can involve a device that can dispense and minimize the efforts required to take the drug and to help track drug usage. Another embodiment can optionally involve stronger controls on the use of the controlled substance, for example, in one embodiment of the present invention, adding one or more abuse-preventing agents to a controlled substance may be an effective way to achieve abuse-deterrence as well as compliant prescribed use of the product and to make the use of the product safer in an environment where children are present. One or more additives or abuse-preventing agents are included in the formulation to render it unpalatable, unusable, unsafe or identifiable as described below, and therefore of no value for illegitimate use. For prescribed use, the abuse-preventing agent can also ensure the patient will use a dispensing machine that can substantially reduce dosing errors and ensure compliant use of the product. These protections are useful to ensure child safety, illegal use and noncompliance. A controlled substance can include Xyrem® or other drugs such as opioids, like morphine among other compounds.

Other methods and formulations described below to achieve the same effect include the use of dyes or colorants that use different forms of the drug or controlled substance, and chemical or structural modification of the above compounds including the drug or controlled substance. There can be concerns with access to Xyrem® in the distribution chain, but other embodiments also include one or more process steps to help prevent abuse and misuse of a drug such as a controlled substance.

One particular embodiment uses Xyrem® as the controlled substance. It is sold as an oral solution of sodium oxybate, a Schedule III controlled substance that has a novel distribution system intended to limit diversion. Xyrem® is commercially available from Jazz Pharmaceuticals and it is also known as gamma hydroxybutyrate, GHB, or sodium oxybate (and other salts) and can be used interchangeably in this application. It is provided in a concentrated solution (500 mg/mL sodium oxybate) and diluted by the patient prior to administration. Once the Xyrem® is delivered to the patient, there is no further means other than physical security to prevent theft or accidental or intentional use by others with access. In addition, there is no means to ensure that the patient has correctly prepared only the prescribed dose, and to prevent preparation of multiple doses more frequently than prescribed.

GHB is made by a variety of processes. It can be synthesized from a precursor compound, such gamma butyrolactone (GBL). See U.S. Pat. No. 3,051,619, see also www.erowid.org/chemicals/ghb/ghb_synthesis.shtml for an example in the popular literature. This link suggests adding a dye to identify this otherwise colorless solution. There are other methods to make GHB, such as microbial production, see EP 2534141 A1, among others.

As stated above, drugs are classified as controlled substances due to their potential for abuse. The FDA requires that some of these drugs or medications be subject to a risk evaluation and mitigation strategy (REMS) to reduce their potential for abuse, misuse or diversion. These REMS processes can be instituted to control distribution for and access to these drugs or medications (either term can be used). Examples of REMS processes are shown in the following U.S. Patents which are hereby incorporated by reference in their entireties: U.S. Pat. Nos. 7,765,106; 7,765,107; 7,668,730; 7,797,171; 7,895,059; and 8,457,988. In one embodiment, a medication that may be subject to a REMS process includes Xyrem®. Xyrem® and its formulations are shown in the following U.S. Patents and Applications which are hereby incorporated by reference in their entireties: U.S. Pat. Nos. 8,591,922; 8,772,306; 6,472,431; 6,780,889; 7,262,219; 7,851,506; 8,263,650; 8,324,275; 8,461,203; 8,461,197; Ser. Nos. 13/739,886; 13/872,997; 13/873,000; and Ser. No. 13/837,714. Every U.S. Patent or Application and every article or citation is also hereby incorporated by reference in its entirety for all purposes. An example of a U.S. patent that describes the use of denaturants in medications is shown in U.S. Pat. No. 6,136,864.

In accordance with one embodiment, the present invention comprises two or more steps or features which serve to make it more difficult to abuse or misuse a prescription drug. For example, people who abuse drugs are less likely to do so if two, three, or four or more impediments to abuse or misuse are employed. These impediments are detailed below, but include materials added to the drug (i.e. additives, aversive agents, denaturants, dyes and the like), chemical changes to the active ingredient or the abuse-preventing additive, or the use of a device to remove the abuse-preventing additive, for example.

One embodiment of the present invention can be useful in the following circumstances: diversion, such as the theft of product; transfer from legitimate patient to someone else (common problem with opioids and stimulants), can be single dose or whole prescription; abuse, such as modifying administration for enhanced effect, crushing, snorting, IV, etc.; over-use, such as patient escalating dosing (common problem with opioids); intentional use differing from prescription, such as patient tinkering, self-optimization without doctor involvement; and unintentional misuse, such as dosing errors. Current approaches focus almost exclusively on abuse, which is not necessarily the biggest problem, but can be easier to address with a formulation.

A problem for most medications that have abuse potential is safety around dosing especially if the dosing is complicated. Instructions for Xyrem® require the patient to draw a particular dose from the bottle into a graduated syringe, dilute it with 60 mL of water and self-administer. The instructions also require the patient to prepare a second dose in similar fashion, and store it for administration after 2-4 hrs. Not many medications require that much patient involvement and errors can occur in drawing the dose or in carrying out steps out of order. Double dosing, or over dosing may occur due to misunderstandings of instructions, and the diluted product or bottle may be available to others, e.g. while the patient sleeps.

One embodiment of the present invention provides a solution for safely using Xyrem® which includes automatic dispensing. In some embodiments, the dispensing and dilution can be automated with a device or machine. For example, a prescription is entered in at a pharmacy or uploaded by physician; the patient receives the amount of Xyrem® consistent with the prescription, such as only the dose that is prescribed and only when prescribed, i.e., bedtime and 2-4 hrs. later, and only to whom prescribed (passive authentication). The patient places a bottle containing a liquid solution of Xyrem® into a device or machine (either inserting the whole bottle, or by pouring the contents into reservoir in the machine); a dispenser enforces the dosing regimen with lockouts and programming. The device can be physically locked for security or it can be used on-demand so that there is no unsecured dose during the night. Physical locks are known in the art and include locks that are built into the device or attached to the outside of the device. Electronic locks include software or non-software devices. They can be employed to shut out a non-authorized user. This device can achieve a level of control not possible with other means as it achieves most elements of safety, but is inadequate for security/diversion. A drug product requiring an in-home dispenser enables a more robust binary solution to security with or without an aversive noted below.

In accordance with one embodiment of the invention, one or more abuse-preventing additives, such as aversive agents, denaturants or dyes or other features as described herein, are included in a liquid formulation of a medication that can be abused and which is distributed to the patient. The additives are selected such that they impart certain characteristics to the formulation, such as undesirable aesthetic changes, negative physiologic impacts, or tracing agents. These include as examples (a) objectionable taste or odor with a denaturant, (b) negative physiological impact such as emesis or flushing, (c) counteraction of effect with an antagonist, (d) color additives rendering the liquid unappealing or unsuitable for surreptitious administration, or (e) persistent dye either in the mouth or in the urine which would be a means of confirming unauthorized use. In addition to the additives, a dispensing device is provided to the patient so that the abuse-preventing additive(s) are removed prior to administration. With this multi-part approach, the formulation is undesirable if diverted from the patient and cannot be prepared by anyone other than the patient, and only in the quantities and regimen programmed into the device.

In one embodiment the removal of the abuse-preventing additive can be implemented as a module in the dispensing device using one or more technologies depending on the properties of the additive. The device can use, for example, activated carbon adsorption, a cation exchange resin, an anion exchange resin, ion chromatography, sorption on clays, silica, or alumina, photochemical reaction (UV lamp), filtration; osmosis or ultrafiltration; separation by selective precipitation induced by common ion additives or other means, or by chemical reaction. Preferably, it should be easy to do with a purpose-built machine, but hard to do in, e.g., a kitchen.

In one embodiment the device can also be used with or without an aversive agent to dispense single doses to limit the amount of drug provided at any one time. Another embodiment can also contain software to provide doses at the appropriate time which can be electronically linked to a prescriber who can remotely adjust and monitor the dose for the patient. It can be used as one component of a multi-part system.

In another embodiment, the abuse-preventing additive can have certain properties that make it undesirable to someone who will misuse the medication and the abuse-preventing additive should be difficult to separate from the medication. The abuse-preventing additive can be a denaturant which will have properties that make it undesirable to misuse, abuse or divert the medication from its legally intended use. In some embodiments of the present invention, the undesirable effect includes an unpleasant taste, smell, emetic effect, or flushing, for example.

In one embodiment, an abuse-preventing additive or denaturant is used that is difficult to separate from the medication, prodrug, or precursor compound (the words "drug" or "medication" can be used for any of the above compounds that can be abused) by virtue of its size, solubility, charge, or any of a number of other physical attributes may allow the compounds to be separated from one another.

In one embodiment, as an example, differential solubility of the abuse-preventing additive and drug in various solvents is a physical property that may complicate or preclude the separation of a denaturant from a medication. An abuse-preventing additive having similar solubility during each of these steps would be difficult or impossible to separate from the medication. Depending on the chemical structure of the abuse-preventing additive, it may or may not be substantially altered by the addition of base or acid or by exposure to aqueous or lipophilic solvents. What is desirable is that at each step of the purification process, the solubility of the abuse-preventing additive (in whatever form) parallels that of the medication. Solubility may be quantified by means of solubility constants for particular solvents, for example, as set forth in The Handbook of Chemistry and Physics, 77th edition, copyright 1996. In particular non-limiting embodiments, the solubility constant for the abuse-preventing additive at each step of the purification process may vary from the solubility constant of the medication by +/−0.50 percent or less, preferably +/−0.30 percent or less, more preferably +/−0.20 percent or less, and still more preferably +/−0.10 percent or less. These variances may differ from step to step of the purification process.

Types of Drugs

In one embodiment of the invention, the drugs or medications that are part of the formulation have the potential for abuse or misuse. One preferred compound is sodium oxybate, sold commercially as Xyrem®, but there are many others that may benefit from the present invention.

For example, the substances include controlled substances which are listed in 21 USC § 812, which is hereby incorporated by references in its entirety. These drugs include: Acetylmethadol; Allylprodine; Alphacetylmathadol; Alphameprodine; Alphamethadol; Benzethidine; Betacetylmethadol; Betameprodine; Betamethadol; Betaprodine; Clonitazene; Dextromoramide; Dextrorphan; Diampromide; Diethylthiambutene; Dimenoxadol; Dimepheptanol; Dimethylthiambuten; Dioxaphetyl butyrate; Dipipanone; Ethylmethylthiambutene; Etonitazene; Etoxeridine; Furethidine, Hydroxypethidine; Ketobemidone, Levomoramide; Levophenacylmorphan; Morpheridine; Noracymethadol; Norlevorphanol; Normethadone; Norpipanone; Phenadoxone; Phenampromide; Phenomorphan; Phenoperidine; Piritramide; Propheptazine; Properidine; Racemoramide; Trimeperidine; Acetorphine; Acetyldihydrocodeine; Benzylmorphine; Codeine methylbromide; Codeine-N-Oxide; Cyprenorphine; Desomorphine; Dihydromorphine; Etorphine; Heroin; Hydromorphinol; Methyldesorphine; Methylhydromorphine; Morphine methylbromide; Morphine methylsulfonate; Morphine-N-Oxide; Myrophine; Nicocodeine; Nicomorphine; Normorphine; Pholcodine; and Thebacon.

A more comprehensive listing of US DEA controlled substances is http://www.deadiversion.usdoj.gov/schedules/orangebook/c_cs_alpha.pdf, incorporated here by reference.

Substances that are not scheduled but are nonetheless controlled are referred to "List" chemicals. Many of these are solvents or precursors with legitimate industrial uses that can also be used to manufacture controlled substances, or legitimate medicinal products such as pseudoephredine that can also be converted to controlled substances but have limited abuse potential in their own right. Such a listing can be found at http://www.deadiversion.usdoj.gov/schedules/orangebook/f_chemlist_alpha.pdf, incorporated here by reference.

Types of Abuse-Preventing Additives

The toxicological or pharmaceutical properties of the additives are often an important consideration. Ingestion of the formulation with the abuse-preventing additive by unauthorized use or abuse should be extremely unpleasant preferably without compromising safety of the mis-user. This is particularly important when, as in the case of Xyrem®, the main intent of the aversive or abuse-preventing system is to deter or prevent accidental ingestion by children. For this reason, many of the embodiments include abuse-preventing additives or agents that are safe. However, in other embodiments where deterring abuse is paramount, it may be preferable to include abuse-preventing additives for which safety has not been proven but effectiveness as an aversive is superior.

One embodiment of the present invention uses abuse-preventing additives to reduce misuse, abuse or diversion of medications as described above. In one embodiment, abuse-preventing additives can be aversive agents or denaturants. Abuse-preventing can also include compounds that are colored dyes to indicate that the medication is controlled or the abuse-preventing additive can be a denaturant or aversive agent that generally renders the composition unsafe or undesirable for ingesting. In an embodiment of the present invention, denaturants used according to the invention may be compounds which are, or become odoriferous in the formulation or during purification and/or synthesis. The odor is preferably unpleasant and pungent. The odor may exist in the formulation or be released during its preparation and thereby render such preparation distasteful and/or serve as a recognizable signal to law enforcement that the controlled substance is being prepared at a particular location.

In certain non-limiting embodiments of the invention, the odor-producing denaturant may contain sulfur, such that a sulfurous odor may be produced during purification/conversion. Non-limiting examples of such sulfur-containing odor-producing denaturants include magnesium sulfate, sodium sulfate, the acid salts of sulfur-containing amino acids such as methionine HCl, ethyl cysteine HCl, ethyl methionine HCl, methyl cysteine HCl and methyl methionine HCl, and thiol containing compounds. When such sulfur-containing compounds are subjected to illegal reaction conditions, odoriferous hydrogen sulfide, low molecular weight mercaptans and/or sulfur dioxide will be produced.

In other non-limiting embodiments of the invention, the odor-producing denaturant may contain nitrogen. Examples of such nitrogen-containing odor-producing denaturants include ammonium chloride, ammonium sulfate, mono, di and trialkylamine hydrochlorides, succinamide and glutaric acid diamide. When such nitrogen-containing compounds are subjected to illegal reaction conditions, odoriferous ammonia, low molecular weight amines and low molecular weight diamines such as putrescine and cadaverine can be produced. For example, the foregoing nitrogen-containing denaturants can develop their unpleasant odor during the alkaline extraction and isolation steps of the conversion process of GBL to GHB.

During the manufacturing process or in the distribution, one or more abuse-preventing additives or agents are added to the formulation to render the product undesirable. An active pharmaceutical agent can be rendered undesirable by the presence of and objectionable taste or pungent odor, or by the addition of antagonists which prevent the desired effect produced by abuse of the drug, and/or which provide an undesirable physiological response. Objectionable taste can be achieved by use of a bittering agent. A non-limiting list of suitable bittering agents include denatonium salts such as denatonium benzoate or denatonium saccharide; sucrose octaacetate; quinine; flavonoids such as quercetin and narigen; and quassinoids such as quassin and brucine. Ideally, the bittering agent should be potent enough so that it cannot be masked with a sweetener. In one embodiment, a particularly suitable bittering agent is denatonium benzoate, which has a bitterness threshold of 0.05 ppm and renders a liquid undrinkable at levels between 20 and 50 ppm [Final Report Study of Aversive Agents, Consumer Product Safety Commission United States of America. 18 Nov. 1992. http://www.cpsc.gov/LIBRARY/FOIA/foia99/os/aversive.pdf. Retrieved 29 Aug. 2013]. A nonlimiting list of suitable agents that impart pungent odors include capsaicin and its analogs, piperine (black pepper), oil of mustard, and resinferatoxin. Other possible additives suitable for producing an aversive effect include long-chain aldehydes and ketones, mercaptans, and aliphatic amines and diamines.

In some embodiments, the denaturant used for alcohol can be used in the present invention. A list of these denaturants can be found at 27 CFR § 21.151 which is incorporated by reference. A partial list of denaturants include: Acetaldehyde; Acetone; Acetaldol, Alpha Terpineol; Ammonia, aqueous; Ammonia solution, strong, N.F; Anethole, N.F; Anise oil; N.F; Bay oil (myrcia oil), N.F.XI; Benzaldehyde; N.F; Benzene; Bergamot oil, N.F.XI; Bone oil (Dipple's oil); Boric acid, N.F; Brucine alkaloid; n-Butyl alcohol; tert-Butyl alcohol; Camphor, U.S.P; Caustic soda, liquid; Cedar leaf oil, U.S.P.XIII; Chloroform; Chlorothymol, N.F.XII; Cinchonidine; Cinchonidine sulfate, N.F.IX; Cinnamic aldehyde (cinnamaldehyde), N.F.IX; Cinnamon oil, N.F; Citronella oil, natural; Clove oil; N.F; Coal tar, U.S.P; Denatonium benzoate, N.F.; Diethyl phthalate; Ethyl acetate; Ethyl ether; Eucalyptol, N.F.XII; *Eucalyptus* oil, N.F; Eugenol, U.S.P; Formaldehyde solution, U.S.P; Gasoline; Glycerin (Glycerol), U.S.P; Green soap, U.S.P; Guaiacol, N.F.X; Heptane; Hydrochloric acid, N.F; Iodine, U.S.P; Isopropyl alcohol; Kerosene; Kerosene (deodorized); Lavender oil, N.F; Menthol, U.S.P; Mercuric iodide, red, N.F.XI; Methyl alcohol; Methylene blue, U.S.P; Methyl isobutyl ketone; Methyl n-butyl ketone; Methyl salicylate, N.F; Mustard oil, volatile (allyl isothiocyanate), U.S.P.XII; Nicotine solution; Nitropropane, mixed isomers of; Peppermint oil, N.F; Phenol, U.S.P; Phenyl mercuric benzoate; Phenyl mercuric chloride, N.F.IX; Phenyl mercuric nitrate, N.F; Phenyl salicylate (salol), N.F.XI; Pine needle oil, dwarf, N.F.; Pine oil, N.F.; Pine tar, U.S.P; Polysorbate 80, N.F; Potassium iodide, U.S.P; Pyridine bases; Pyronate; Quassia, fluid extract, N.F.VII; Quassin; Quinine, N.F.X; Quinine bisulfate, F.XI; Quinine dihydrochloride, N.F.XI; Quinine sulfate, U.S.P; Resorcinol (Resorcin), U.S.P; Rosemary oil, N.F. XII; Rubber hydrocarbon solvent; Safrole; Salicylic acid, U.S.P; *Sassafras* oil, N.F.XI, Shellac (refined); Soap, hard, N.F.XI; Sodium iodide, U.S.P; Sodium, metallic; Sodium salicylate, U.S.P; Spearmint oil, N.F; Spearmint oil, terpeneless, Spike lavender oil, natural, Storax, U.S.P; Sucrose octaacetate; Thimerosal, U.S.P; Thyme oil, N.F.XII; Thymol, N.F; Tolu balsam, U.S.P; Toluene; Turpentine oil, N.F.XI; Vinegar; and Zinc chloride, U.S.P.

Antagonists can be employed as additives in formulations containing a drug that acts as an agonist to the same receptor. Antagonists are well-known for opioids, and include naltrexone and naloxone. Flumazenil is an antagonist for benzodiazepines. An antagonist for GHB is 6,7,8,9-tetrahydro-5-hydroxy-5H-benzocyclohept-6-ylideneacetic acid (NCS-382).

Sometimes when a suitable antagonist is not available, a pharmaceutical agent having an effect that is counter to, undesirable or inconsistent with the purpose of abuse may be added in its place. For example, methylphenidate is often abused for its stimulant properties in people without ADHD, often to prolong alertness for study or other tasks. To prevent misuse for that purpose, a mildly sedating agent such as an over-the-counter sleep aid or sedating antihistamine can be added to the formulation and subsequently removed by the dispensing machine in an environment of legitimate use. Similarly, benzodiazepines and non-benzodiazepine hypnotics may be less desirable for abuse if mixed with a high dose of caffeine. Although a benzodiazepine antagonist exists (flumazenil), it is relatively short acting whereas caffeine, which is not a true antagonist, has much longer duration of an effect that runs contrary to the desired effect of the drug.

Abuse-preventing additives producing undesirable physiological responses include niacin (flushing reaction), ipecac (emesis) and the like. Pfizer and Acura Pharmaceuticals created an Oxycontin® formulation containing niacin.

One or more additional agents can be optionally added to facilitate detection of an unauthorized use. For example, a staining dye such as gentian violet can be added such that, if present when ingested, the user's mouth will be stained for several days thereafter. Alternatively, methylene blue added to the formula will color the urine blue. Other dyes are commercially available at sources such as Birko, Co. (birkocorp.com), and are also suitable. Also, dyes, pigments, or other coloring agents can help indicate that the medication is being used surreptitiously to unsuspecting persons. A full list of color dyes and additives approved by the FDA for use in drugs, including drugs generally as well as ingested drugs, is available at 21 C.F.R. § 73, subpart B and § 74, subpart B. The dyes or pigments listed in 21 C.F.R. § 73, subpart B, include alumina (dried aluminum hydroxide); annatto extract; calcium carbonate; canthaxanthin; caramel; beta-carotene; cochineal extract; carmine; synthetic iron oxide; mica-based pearlescent pigments; talc; and titanium dioxide. The dyes listed in 21 C.F.R. § 74, subpart B, include FD&C Blue No. 1; FD&C Blue No. 2, FD&C Green No. 3; D&C Green No. 5; FD&C Red No. 3; D&C Red No. 6; D&C Red No. 7; D&C Red No. 21; D&C Red No. 22; D&C Red No. 27; D&C Red No. 28; D&C Red No. 30; FD&C Red No. 40; FD&C Yellow No. 5; FD&C Yellow No. 6; and D&C Yellow No. 10.

A non-staining coloring agent can be added to facilitate detection of the surreptitious administration in beverages. Finally, a removable colorant can be selected based on its physical or chemical properties in light of the device-facilitated treatment technique, such that lack of color would indicate to the legitimate patient that the solution has been effectively treated to remove the additives, such as those additives whose presence are not made obvious by e.g., their color, smell or taste.

As mentioned above, more than one additive may be used. For example, 2, 3, 4, 5, 6, 7, or more additives or features can be used simultaneously or sequentially. A formulation of a medication can have more than one additive that performs the same function, or the additives can have different mechanisms of action. For example, two additives can be odorous, or one can have an odor and another may provide a visual indication. Multiple combinations of odor, bitterness, dye, chemical action or other types of additives can be used for purposes of the present invention.

The drug formulation may include a combination of one or more additives or features to enhance security and prevent improper uses and misuse. Other features can include security measures implemented on the device, access to the device, chemical changes in the drug and other features mentioned in the present application.

As many pharmaceutical agents are intensely bitter in their own right, an aversive agent may not be required in some embodiments. In such a case, the formulation additives that ordinarily would be present to make the product palatable, such as flavors and sweeteners, would simply be omitted. Instead, as part of dispensing in the environment of legitimate use, such additives would be imparted in the dilution step prior to administration. An example of this would be codeine cough syrup, which often contains glycerol, sorbitol, and sodium saccharin or other sweeteners to make it palatable. Such sweeteners would instead be omitted, and the water for dilution in the dispenser would have the sweetener in it.

Bitterants

Sucrose octaacetate is a widely used aversive agent. It is the active ingredient in nail biting and thumb sucking deterrents. Due to its negative Log P (partition coefficient), it would not be easily separated from Xyrem® or GBL by extraction or carbon treatment. From that standpoint, it is an attractive complement to another aversive agent that is amenable to carbon treatment, such as capsaicin. Sucrose octaacetate can be removed by reaction in lime (calcium hydroxide) among other methods. An advantage of using lime is that very little reagent would be needed, and the solubility of lime in water is sparing—the patient could drink the treated product without titration back to neutral pH.

According to the US Consumer Products Safety Commission (CPSC), sucrose octaacetate is detectable at 10 ppm, and levels of 600 ppm will render a substance inedible. Its solubility in water is 900 ppm, so may be effective in Xyrem® without including a solubilizer in the formulation.

The chemical structure for sucrose octaacetate (Fully acylated sucrose) is shown below:

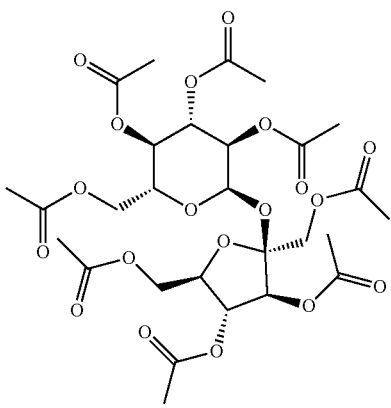 [SMILES: CC(=O)OC[C@H]1O[C@@](COC(C)=O)(O[C@H]2O[C@H](COC(C)=O)[C@@H](OC(C)=O)[C@H](OC(C)=O)[C@H]2OC(C)=O)[C@@H](OC(C)=O)[C@@H]1OC(C)=O]

Sucrose octaacetate has the following characteristics: PubChem: http://pubchem.ncbi.nlm.nih.gov/summary/summary.cgi?cid=31340; MW 678.6; Log P: −0.9; aqueous solubility: about 900 ppm. Some key features include: it is a large molecule, so it can be osmotically separated from GHB; it is very soluble in alcohols; Liability for stability (ester cleavage in water); it is safe—doses of 5 g/kg are not lethal; and it is widely used.

An alternative bittering agent is denatonium (benzoate or saccharide) which can be detectable at 0.01 ppm and is effective at levels of about 20 ppm. It can be difficult to reduce the concentration of denatonium below 0.01 ppm, which may leave some bitter taste after the removal process. However, complete elimination of the bitterant is not necessary, as long as it can be countered by conventional formulation techniques such as adding a sweetener in the diluting medium.

The stability of sucrose octaacetate is analogous to triacetin (fully acylated glycerol). Triacetin is stable only around pH 4. It has a half-life at pH 7 of 60 days in water at 25° C., and at pH 9, it is <1 day. In one embodiment, sucrose octaacetate is used in a formulation having a pH where the sucrose octaacetate is stable. In another embodiment, the controlled substance can be formulated such that the sucrose octaacetate is not rendered unstable. In another embodiment the bitterant, such as sucrose octaacetate, can be added to a different form of the controlled substance. For example, the GBL form can be employed instead of sodium oxybate (GHB). This would result in remarkable stability, and also extend the amount of bitterant that is used. Also, stability may not be a significant issue in situations where the bitterant will be used within a short period after addition. In that case, the use of a central pharmacy can be employed to add the agent prior to shipment and the formulation can be expeditiously delivered for immediate use.

Pungent Agents

In some embodiments of the present invention, potential pungent agents that can be used include resinferatoxin, capsaicin, piperine, and allyl isothiocyanate. Piperine is the agent in black pepper, capsaicin is found in chili peppers and allyl isothiocyanate is found in horseradish and wasabi.

Piperine (Black Pepper)

The structure for piperine is shown below.

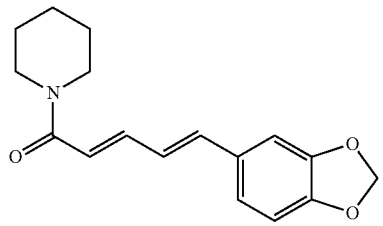 [SMILES: O=C(/C=C/C=C/c1ccc2c(c1)OCO2)N1CCCCC1]

Piperine has the following characteristics: Pubchem cid=638024; MW 285.3; Log P=3.5; Water solubility 40 ppm; and soluble in alcohol. Piperine has the following features: it has a threshold of effect of about 1.35 ppm; no aversive level given, but a pungency about 15% that of capsaicin.

Capsaicin

The structure for capsaicin is shown below:

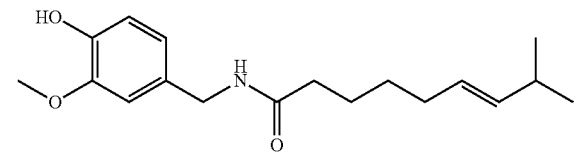 [SMILES: COc1cc(CNC(=O)CCCC/C=C/C(C)C)ccc1O]

Capsaicin has the following characteristics: Pubchem cid=1548943; MW 305.4; Log P=3.6; water solubility ~10 ppm; and soluble in alcohol. Capsaicin has the following features: it has a threshold of effect of about 0.02 ppm; and no suggested level for aversives.

Both agents are very lipophilic, and therefore are excellent candidates for activated carbon removal. Piperine is 70 times less potent than capsaicin as defined by threshold of taste, and about 6 times less potent as defined by relative pungency.

Determining the required level of capsaicin for abuse deterrence can vary as people can tolerate different amounts. A benchmark is Tabasco sauce, which is about 150 ppm capsaicin (2500 Scoville units). Capsaicin can be added to a controlled substance at levels above 150 ppm, 200 ppm, 250 ppm, 300 ppm, 350 ppm or more. If capsaicin is added at a level of 150 ppm in an aqueous formulation of a controlled substance such as Xyrem®, this can exceed the solubility limit, so one of two approaches can be used: the use of a solubilizer, or the use of a suspension.

The appropriate levels of other additives may be determined based on taking the typical tolerated dose and increasing it to a level that inhibits abuse. For example, piperine can be employed a level of more than 1,000 ppm, 1,300 ppm, 1,500 ppm, 1,700 ppm or more. Allyl isothiocyanate can be present at a level 2, 3, 4, 5, or 6 times higher than is normally present in wasabi.

In the event that solubilizers are used, examples are as follows: propylene glycol, PEG 3350, HP-beta-cyclodextrin and many other solubilizers can be added. In one study, a 50-fold increase in saturated solubility was achieved by using 1:1 molar cyclodextrin—a conservative ratio. With that, required solubility could be achieved with only 0.08% HP-beta-cyclodextrin added to Xyrem®.

Other solubilizers that might be employed, which likely will not substantially impede removal of the capsaicin or other aversive by activated carbon adsorption, include (but not limited to): PEG-400, triacetin, triethyl citrate, ethanol, DMSO, glycol ethers such as diethylene glycol monoethyl ether, glycofurol.

Of the two approaches, a suspension may be preferred if a re-usable carbon filter is employed to remove the solvated capsaicin. With a suspension, a far higher level of capsaicin can be added to the formulation without reducing the service life of the carbon bed. A further refinement would be to add a solubilizer, such as triacetin or triethyl citrate, which is hydrolysable under highly alkaline condition that does not destroy sodium oxybate or the target therapeutic agent. In this instance, the solubilizer may be effectively removed by hydrolysis in a pre-treatment step, resulting in precipitation of much or most of the capsaicin prior to carbon treatment to remove the remaining dissolved capsaicin. One skilled in the art will recognize that a suspension requires creating of fine particles and formulating a medium capable of suspending the particles for a useful period of time, often through manipulation of viscosity and surface tension.

Dye or Stain

A dye or stain serves several purposes either alone or in combination with another additive or aversive agent. The dye makes it more difficult for surreptitious administration, due to visual detection. FDA-approved color additives for drugs are useful to prevent such surreptitious administration. Also, a dye may indicate that someone has used the product, if detection is useful. Finally, when run through the treatment and dispensing machine, lack of color in the diluted product can be a positive indication of successful removal of another additive. Ideally, the dye is selected so that the overall treatment process is least effective for dye removal. That way residual color in the diluted dose is an advance indication that the treatment module needs to be replaced or rejuvenated.

Carbon filtration is an example of a suitable method of removing dyes. Blue dyes are considered for liquids like Xyrem®, since blue is least prevalent in beverages. Gentian violet was evaluated in laboratory studies. A 200 ppm solution of Gentian violet in water is intensely violet, and creates a relatively persistent stain on the skin. This 200 ppm solution was treated with 0.2% slurry of activated carbon for about 10 minutes, and then filtered. Although the treated solution was not entirely color-free, it was practically without color. By visual comparison with diluted standard, about 99.5% of the Gentian violet was removed by this process. A more efficient carbon treatment, as with a filtration cartridge vs. suspended carbon, would provide more complete color removal, for example total color removal.

Gentian Violet (Crystal Violet)

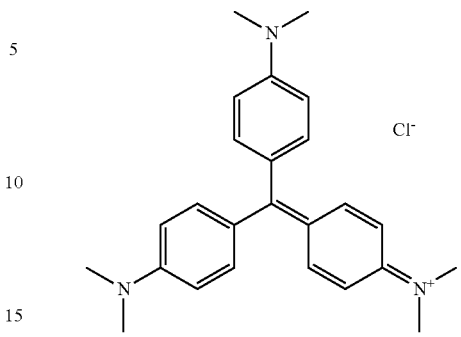

Gentian Violet has the following characteristics: PubChem CID: 11057; MW 408; soluble in water; Anthelmintic, topical treatment of thrush, no longer widely used; and Gram stain, will color mucosal surfaces and skin.

Methylene Blue

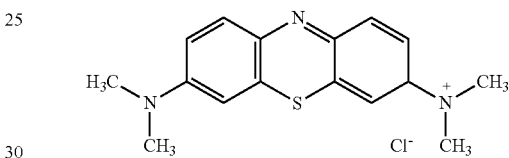

Methylene Blue has the following characteristics: PubChem CID: 6099; MW 319.9; soluble in water; Molar extinction 95,000 M-1 cm=1; and at modest doses, turns urine blue.

Brilliant Blue (FD&C Blue 1, D&C Blue 4)

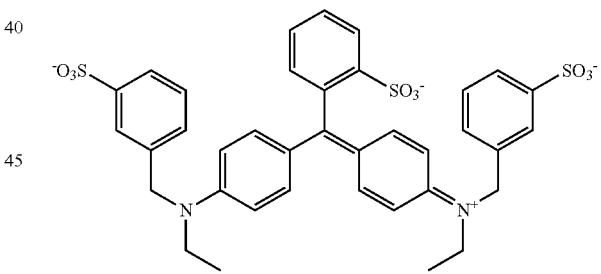

Brilliant Blue has the following characteristics; PubChem CID: 19700; MW 760.9; water-soluble; Molar extinction 138,000 M-1 cm-1; and is acceptable in food and pharmaceuticals.

Methylene blue is commonly used to benchmark carbon filtration modules. Carbon loading achieved with 200 ppm methylene blue is about 400 g/m$^3$ surface area, which translates to a capacity of about 1 g for a typical filtration cartridge that may be suited to use in an in-home dispenser (3M bioCap). Hence, unless a higher capacity or multiple carbon filter cartridges are used, the concentration of dye has a predictable impact on service life (about 1.5 years at 100 ppm, 0.75 years at 200, 3 years at 50 ppm, etc.)

Methylene blue is approved for IV use and its carbon sorption is already characterized. It also has higher color intensity for the same mass concentration.

Form and Formulation

Using GHB as an example, its precursor (GBL) (without diluent) has vastly different properties, is essentially bioequivalent on a molar basis, and is cleanly converted to high-purity oxybate in a simple one-step reaction. Many of the formulation challenges—particularly around stability and solubility—can be solved by considering neat GBL as the drug product that is shipped to the patient. The GBL can then be converted, aversive additives removed, diluted, and dispensed in a form that is palatable and otherwise meets specifications for a sodium oxybate solution.

Ideally, the aversive system works with Xyrem® or any other salt or mixture of oxybate or other controlled substances.

In some embodiments, the viscosity of the formulation may be advantageously modified. For example, if a suspension is used for formulations of the present invention containing capsaicin or other aversive, then viscosities much higher than that of water are advantageous to provide a more stable suspension.

A higher viscosity, for example about 80-100 cP, may be useful in order to deter use of off-the-shelf water filtration (Britta filters) to remove the aversive agent. At a high enough viscosity, the processing time through an off-the-shelf gravity-fed filter renders it extremely impractical and thus discourages abuse.

Higher viscosity formulations are also advantageous if the patient is making fluid connections in the dispenser, e.g. by changing out supplies because connections in the dispenser are less likely to leak. Even factory-made fluid connections will be more reliable with modest increases in formulation viscosity.

Higher bulk viscosity compositions are also less attractive or more difficult to ingest by potential abusers. In addition, if a dye is used in the formulation, higher bulk viscosity also results in much less mess if some solution is spilled.

Viscosity can be increased by the addition of a water-soluble polymer, or by use of fumed silica. fumed silica is less desirable in embodiments in which the dispenser includes a filter cartridge, because fumed silica may cause fouling. The selection of an appropriate polymer depends on whether it is also used to solubilize the aversive agent, such as capsaicin. If capsaicins are present, then a large amount of low-molecular weight polymer is desirable. If not, then a small amount of high molecular weight polymer is desirable. Suitable polymers include, for example, polyethylene oxide, sodium carboxymethyl cellulose (CMC), and guar gum. The use of a polymer with a dispenser including a filtration module would not be problematic, as long as the polymer doesn't block the pores of the filter media.

To create a liquid suspension, capsaicin is adsorbed onto a fine carrier, such as neusilin or fumed silica, then dispersed in high shear mixer. When a higher viscosity product is desirable, a stable suspension is relatively easy to prepare, and the stability of the capsaicin is also improved, since most of it is undissolved (and thus not prone to hydrolysis). The life of a carbon filter module would be extended as well, since most of the capsaicin would be removed by the cellulosic pre-filter.

Device

The device (also referred to as a dispensing device, a dispenser, and variants thereof) can be employed to work with or without an abuse-preventing additive or aversive. In some embodiments, an abuse-preventing additive or aversive is not used, and the device can facilitate secure, convenient, proper and timely administration of the controlled substance. In some embodiments, the dispensing device can prepare a single dose, optionally diluting with water or other media, and optionally treating to remove the additive(s), perform a chemical conversion, or otherwise permit ingestion. In some embodiments, the device can include a pump (e.g., a peristaltic pump, a plunger of a syringe, a diaphragm, and/or the like) that can dispense the concentrated solution. In some embodiments, the pump is a first pump and the device can include a second pump of similar or different design than the first pump, that dispenses the diluent, and a treatment module in the fluid path containing the formulation. The device can be programmable, and can optionally include lockout features and/or other safety mechanisms to authenticate and control dosing, and can dispense the drug at the time needed during normal operation. The dispensing time for Xyrem® is typically just before sleep for the initial dose and 2.5 to 4 hours later for the second dose. In some embodiments, when the aversive is included, the treatment module can employ one or more techniques to separate the additive(s) from the denatured formulation.

Although the dispensing device may dispense one dose at a time as-prescribed, in some embodiments, the dispensing device can process an entire bottle of concentrated liquid and store it in an internal reservoir, and then subsequently dispense from that reservoir to the patient as-prescribed. Such embodiments can account for the complexity of the process of removal of the additives resulting in long processing times or poor yields unless completed in one large batch. Further, in such embodiments, the device can include a physical security component (e.g., a lock) protecting its reservoirs, in addition to other controls on its normal operation. For example, some products such as Xyrem® (sodium oxybate oral solution, also known as GHB) are provided to the patient in multiple bottles in each shipment. The bottles not in use would still be protected from abuse, and can be kept safely outside the device while the bottle in use would be rendered suitable for ingestion but still under control of the dispensing device.

In one embodiment, the device can communicate with a prescriber via wired or wireless means (e.g., telephone line, wireless modem, cellular device, or the like), and the appropriate times to give the dose(s) to the patient are conveyed to the device by the prescriber. When an aversive is used, the device can be controlled or authorized remotely to process the formulation and to remove the denaturant, or to render it harmless and the formulation palatable. The device can allow access to the medication at particular times, and in appropriate minimal doses, enough to satisfy the current needs of the patient. The device can be authorized for use by the prescriber, pharmacy or other entity that has authority to provide the drug to the patient, thereby preventing unauthorized acquisition of the device and its use.

Other aspects of the device may include a control panel for information display and/or an interface for user input. The control panel can show the number of doses taken that night, time for next dose, actual time, etc. The interface may allow for manual override of some control features, and allow for dispensing multiple doses for travel. The interface would also perform some other functions, such as for setting the time, alarm, number of doses or amount of doses, etc. Also, the interface may include an indicator that a lockout period has lapsed and that another dose can be dispensed, an alarm to wake the patient for a second dose administration, passive authentication such as with infrared emitting diode on a bracelet worn by the patient, active authentication such as with a pincode entered by the patient, a keyed enclosure for secure access to the product, programming controls that govern frequency and amount of administration, data logging of dispensing events, indicators displaying amount of drug treated, dispensed, and/or remaining within the system, programming that can be updated by plug-in chip or cartridge or by remote connection such as a wireless device, and a service life timer or performance measurement and indicator that may prompt the patient to either send the unit for service or replace consumable elements such as filters. Software and/or hardware can control the internal operation of device, including distribution of fluids from the different reservoirs. The software and/or hardware can control the amount of fluid from each reservoir and thus can change the amount of each dose electronically. The dose can be varied as mentioned herein using a wireless or other connection to receive instructions from a prescriber. A balance can be included for measuring out doses by weight or ensuring compliance. See also other devices such as U.S. Pat. Nos. 4,473,884, 4,695,954, 4,971,221, 5,047,948, 5,099,463, 5,200,891, 5,809,997, 5,200,891, 6,148,815 and WO2013040075 which are incorporated by reference in their entireties.

In some embodiments, the dispensing device can include at least a processor and a memory. The dispensing device can include one or more modules for implementing the functionality described herein. As used herein, a module can include, for example, any assembly and/or set of operatively-coupled electrical components, and can include, for example, the memory, the processor, electrical traces, optical connectors, software (executing in hardware), and/or the like.

The dispensing device can be in communication with other entities, such as a device associated with a prescriber as mentioned above, via a network, which can be any type of network (e.g., a local area network or LAN, a wide area network or WAN, a virtual network, a telecommunications network, and/or the internet), implemented as a wired network and/or a wireless network. Any or all communications can be secured (e.g., encrypted) or unsecured, as is known in the art.

It is intended that the devices and methods described herein can be performed by software (stored in memory and/or executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments of the dispenser/dispensing device include two compartments that can be detachable. See FIGS. 1-3 which show functions and features of each compartment (COM1), (COM2) of a dispensing device (100). In some embodiments, COM1 and COM2 are separable and reattachable in any suitable manner such as, for example, via adhesive means, via interlocking components such as, for example, a snap-fit arrangement, a hook and loop arrangement, via magnetic or electromagnetic coupling, and/or the like. COM1 includes a product bag (A) configured to hold the product and a treatment stack (B) configured to treat the product. COM2 include a treatment reservoir (C) configured to hold the treated product, a water reservoir (E) configured to retain/supply water for dilution, a mixer (D) configured to generate a diluted dose of the treated product, and a dilution vessel (F) configured to hold the diluted product. In some embodiments, and as illustrated in FIG. 1, the second compartment COM2 can additionally include a dose receiver (G) for receiving a dose of the diluted product, though in other embodiments (not shown), the dose receiver can be external to the dispensing device 100.

Described herein using the scenario when the product includes aversive additives, during use, the first compartment (COM1) can contain the product, stored in the collapsible bag (A), with the treatment stack (B) above it. The product flows from the bag (A) through the treatment stack (B), where the aversive additives are filtered, retained, and/or otherwise removed to yield a denatured product. The treatment stack (B) is fluidly coupled to the treatment reservoir (C) of the second compartment (COM2) via a line (e.g., a coiled line) connecting stack (B) to the second compartment (COM2), where the reservoir (C) can hold a multi-day supply of the denatured product (also referred to as the treated concentrate). From reservoir (C), the treated concentrate flows through the mixer (D). The mixer (D) can include any suitable components for mixing two or more substances such as, for example, a combination of one or more pumps and one or more valves, where the treated concentrate can be metered and then diluted with water from the water reservoir (E) before flowing into the dilution vessel (F). In some embodiments (not shown), the water reservoir (or a fluid source, like a water pipe from a household source) can be external to the dispenser (DISP), and reference character (E) can denote a port for coupling the external water reservoir to the dispensing device (DISP). In some embodiments, the dilution vessel (F) can hold a single dose and, when requested by the patient and (optionally, when) compliant with software controls, is dispensed to the dose receiver (e.g., a dosing cup) (G). Although shown here as part of the overall dispenser (DISP), it is understood that the dose receiver (G) can be external and/or otherwise not included as part of the dispenser (DISP). In some embodiments, the dose receiver (G) can include a port formed on the dispenser (DISP) for dispensing the single dose to an external dose receiver, such as, for example, a cup.

In some embodiments, such as when the product does not include the aversive, for example, the treatment stack (B) can be optional. In such embodiments, the device (DISP), and the second compartment (COM2) in particular, can still include the treatment reservoir (C), the water reservoir (E) holding water for dilution, the dilution vessel (F) providing additional drug storage, the electronics, the mixer (D) (e.g., piping and valves), and/or the like. In some embodiments, security and/or operational features designed for dispensing the drug can be included in the dispenser (DISP). In some embodiments, a balance (not shown) for weighing out proper doses and to ensure that the proper amount was consumed can be included as part of the dispenser (DISP), or in a kit that include the balance and the dispenser (DISP).

Separate compartments can remove some burden of the patient of needing to service the entirety of the dispenser (DISP). The patient's task includes loading/unloading product, which may require lifting the treatment stack (B). The treatment stack (B) should be easily separable, such as for servicing, or for replacement (i.e., exchanging old for new). If new treatments are introduced, they could be implemented without opening the second compartment (COM2), which can include hardware and/or programming controls as described earlier.

The patient can separate the compartments (COM1), (COM2) for traveling, or can elect to travel with only the second compartment (COM2) operable for dispensing/dilution. For example, if the patient is taking a short trip of 5 days or less, the reservoir (C) of treated Xyrem can hold a sufficient supply for daily dosing for the 5 days, and the first compartment (COM1) is not required.

In some embodiments, the second compartment (COM2) can hold and provide the drug for up to 5 days. If something goes wrong, the first compartment (COM1) can be reattached to the second compartment (COM2) to resupply product without disruption in therapy. It also allows the patient the option of storing the product in a first compartment (COM1) separate from the second compartment (COM2), and joining them to refill the reservoir (C).

The main circuit board can be placed in the second compartment (COM2), such as against a common wall with the first compartment (COM1) and away from any potential leaks. The dispensing device (DISP) and/or the second compartment (COM2) can be plugged into an electrical outlet or can run on rechargeable battery as a main or secondary power supply (e.g., a 12V power supply). A battery is useful to avoid disruption of power during dispensing. The dispenser (DISP) and/or the second compartment (COM2) can check for sufficient battery power before beginning dispensing.

In some embodiments, the dispenser (DISP) has the overall height of the treatment stack (B) to be about 10 centimeters. In one embodiment, the dimensions of the treatment stack (B) are about 10 inches height×10 inches width×6 inches depth. Factors that could potentially affect size of the dispenser (DISP) or any compartment/component thereof can include: using horizontal orientation of treatment stack (B); limiting size of water reservoir (E) which would require the patient to fill more frequently (e.g., more frequently than 1/week); and reducing product bag (A) volume. In some embodiments, the dispenser (DISP) is designed and/or configured such that patient refill the reservoir (C) about once a month, but a smaller size could require refilling about once a week.

Still referring to FIG. 1, the dispensing device (DISP) can also include a controller (CTRL) configured to control operation of the dispensing device. In some embodiments, the controller (CTRL) can be removably coupled to the first compartment (COM1), or to the second compartment (COM2), or both. In some embodiments, the controller (CTRL) is fixedly coupled to at least one of the first compartment (COM1) and the second compartment (COM2). It is intended that coupling between the controller (CTRL) and the compartments (COM1), (COM2) is intended to encompass mechanical coupling, electrical coupling, and/or the like. While illustrated here as a separate component for simplicity, it is understood that aspects of the controller (CTRL) can be more integrally formed with the first compartment (COM1), or the second compartment (COM2), or both.

In some embodiments, the controller (CTRL) can include at least a processor (H) and a memory (I). The controller (CTRL) can further include an input/output interface I/O (J) that can encompass, but is not limited to, interfaces for network connectivity (wired/wireless, including Bluetooth), a display unit, input interfaces (such as selectable keys, a touchscreen, a control panel, and/or the like) for use by the user, and/or the like. The controller (CTRL) can further include a battery component (K) for powering the dispensing device (DISP). In some embodiments, the battery component (K) includes a rechargeable battery, and/or a port for electrical connectivity.

In some embodiments, the controller (CTRL) can optionally (as indicated by dotted reference lines) include a database (L) for storing information including, but not limited to, patient information, dosing information, compliance information, and/or the like. In some embodiments, the controller (CTRL) can optionally include one or more locks (N) to limit access to and/or use of the dispensing device (DISP). The locks (N) can encompass hardware-based lockout mechanisms (e.g., a physical lock, a coded latch, and/or the like) as well as software-based lockout approaches (e.g., password and/or pin-based authentication). In some embodiments, the controller (CTRL) can optionally include one or more indicators (M) for communicating with a user such as, for example a visual indicator (e.g., an LED), an audible indicator (e.g., a beeping sound), a graphic indicator (e.g., an icon), and/or the like. It is understood that the various illustrated components of the controller (CTRL) need not be mutually exclusive: for example, the lock (N) can include password-based authentication that is based on instructions stored in the memory (I) and executed by the processor (H).

In some embodiments, a kit includes the dispensing device (DISP) of FIG. 1 and one or more sets of instructions for dispensing a substance using the dispensing device. In some embodiments, the substance includes Xylem. In some embodiments, the kit can further include one or more product bags containing the substance to be dispensed using the dispensing device (DISP).

In some embodiments, the first compartment (COM1) can be designed and/or operable as described for FIG. 2 below. In some embodiments, the second compartment can be designed and/or operable as described for FIG. 3 below.

Product/Treatment Module

Figure 2:
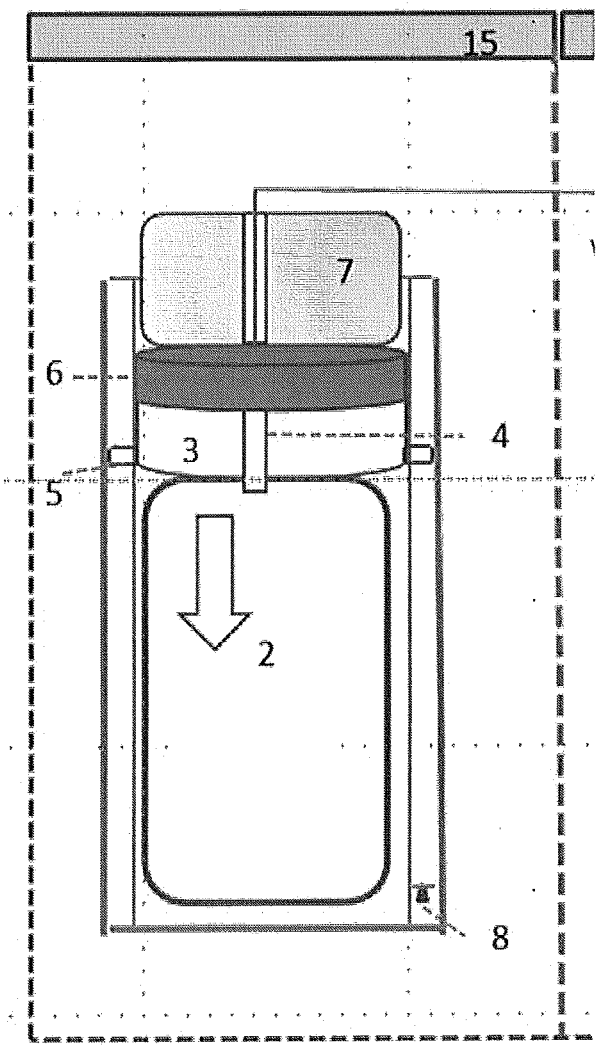
FIG. 2 illustrates an embodiment of the first compartment of FIG. 1.

FIG. 2 shows one embodiment of the invention that includes a case for drug reservoir and treatment (1). In some embodiments, the case (1) is functionally and/or structurally similar to the first compartment (COM1) illustrated in FIG. 1.

In some embodiments, rectangular guides run up the case (1) and can be made of transparent material such as, for example, glass, clear plastic (not shown), and/or the like. The case (1) can include an outer enclosure (not shown) that has a window (not shown) configured to give a patient a visual indication of amount of drug product left in a product bag (2). The drug product is held in a bag (2), which can be similar to a collapsible IV bag that holds about 600 milliliters. In some embodiments, the bag (2) is functionally and/or structurally similar to the product bag (A) of FIG. 1.

In some embodiments, the case (1) includes a collar (3) shaped to fit under a filter module (6) and also partially shroud the bag (2) serves to maintain the integrity and level of the collar (3), the filter module (6), and a cylindrical weight (7) (also collectively referred to as a "head assembly") as each of these components travels during deployment. A cutout (also termed an exit port) (4) in the collar (3) allows connection between the product bag (2) and the filter module (6). A notch (5) in the collar (3) guides into channels cut out in the case (1) for proper placement and for actuation of a pressure switch (8) (also termed a contact switch). The filter module (6) can include any suitable filter configured to remove aversive additives such as, for example, a depth filter having activated carbon elements inside a plastic enclosure. Exemplary activated carbon elements include, but are not limited to 3M Cuno BioCap30 Zeta Plus. In some embodiments, the case (1) includes the cylindrical weight (7) designed with a center-drilled channel for a fluid line provides the necessary pressure for driving flow. The contact switch (and offset limiting notch) (8) is activated by a collar notch (5) indicating to the patient that the drug product bag is empty. In some embodiments, the filter module (6) can be functionally and/or structurally similar to the treatment stack (B). In some embodiments, the combination of the filter module (6)/cylindrical weight (7), can be functionally and/or structurally similar to the treatment stack (B).

In some embodiments, the patient can draw one or more doses (e.g., no more than 36 ml) per day, which can allow the case (1) to treat product for up to 24 h per day without drawing power. Such aspects of the dispensing device (DISP) can enable operation at low pressure drop and with more viscous fluids than would be possible with an on-demand treatment that would require much higher flow rate. In some embodiments, an internal reservoir on the dispenser/diluter side (e.g., the treatment reservoir (C) in the second compartment (COM2) in FIG. 1) can hold up to 3 oz (90 ml) of treated product, and the time required to initially charge the internal reservoir can be a design factor for the case (1). The case (1) can further include a resealable cover (15), such as, for example, a lid that can be snapped in/out of place.

in some embodiments, the filter module (6) is gravity-driven, and can use a collapsible bag containing the drug as product bag (2), a filter apparatus (e.g., the filter module (6)), and a weight above it (e.g., the cylindrical weight (7)) to apply pressure to collapse the bag (2), pushing product through the filter (6) and out to the second compartment (COM2). In some embodiments, such a design can provide a constant pressure drop across the filter apparatus, and can operate consistently regardless of the size of the product bag. The absence of a pump can eliminate the associated problems with flowing a suspension (e.g., potential for clogging inlet valves). Downstream of the filter apparatus, a particle-free product is provided to ensure smooth operation of check valves and pumps.

Still referring to FIG. 2, in some exemplary embodiments, the product is Xyrem provided in collapsible bag (2), similar to a juice bag or IV bag. The size of the bag can be determined by the dimensions of the available filter cartridges for the filter module (6) which, in such exemplary embodiments, can be about 7 cm in diameter. A full month's supply of Xyrem at highest dose is approximately 18 ml×30.5=550 ml, so bag (2) can be about 600 ml volume at 90% full. At 7 cm diameter, bag (2) would be 16 cm tall, or have an aspect ratio of about 2:1. The bag (2) can include the exit port (4) that connects to the filter module (6) in any suitable manner, such as a tapered female connector (e.g., Luer-Lock), a hose barb, and/or the like. The collar (3) can be custom molded to fit around the inlet port and outer surface of the filter module (6), and the cut-out weight cylinder (7) can fit on the outlet port and outer surface of the filter module. A coil of flexible tubing can run from the filter outlet to the dispenser/diluter unit (i.e., similar to fluid coupling between the first component (COM1) and the second component (COM2) in FIG. 1) on the other side of the dispenser (DISP1).

In some exemplary embodiments, the cartridge filter is 3M Cuno BioCap30 with cellulose filter media and activated carbon (about 1 g) filter aid. The filter service life can be between 0.5 and 5 years, depending on the amount of additives and carbon loading achieved with them. In some exemplary embodiments, filters with grades that accommodate higher viscosity as well—up to 80 cP—can be employed.

Still referring to FIG. 2, in some embodiments, the case (1) can include: tabs on the treatment stack collar (3) that trip the pressure switch (8) indicating that the bag (2) is empty; an outer cylinder (not shown) which the whole stack fits into, which can be clear; a window slit (not shown) can be created in the outer enclosure to allow the patient to see movement of the stack (indicating how much product is left). Additionally or alternatively, a visual indicator such as an LED can be included in the tab (5) that travels with the tab, for easier visualization. The treatment stack (e.g., in some embodiments, can be the combination of the collar (3), filter (6), weight (7)) can fit together as one piece. In such embodiments, the patient will need to remove the stack to change out the Xyrem bag. The filter can be changed once a year, or the patient can simply send the entire assembly back for a replacement.

Dilution and Dispensing

Figure 3:
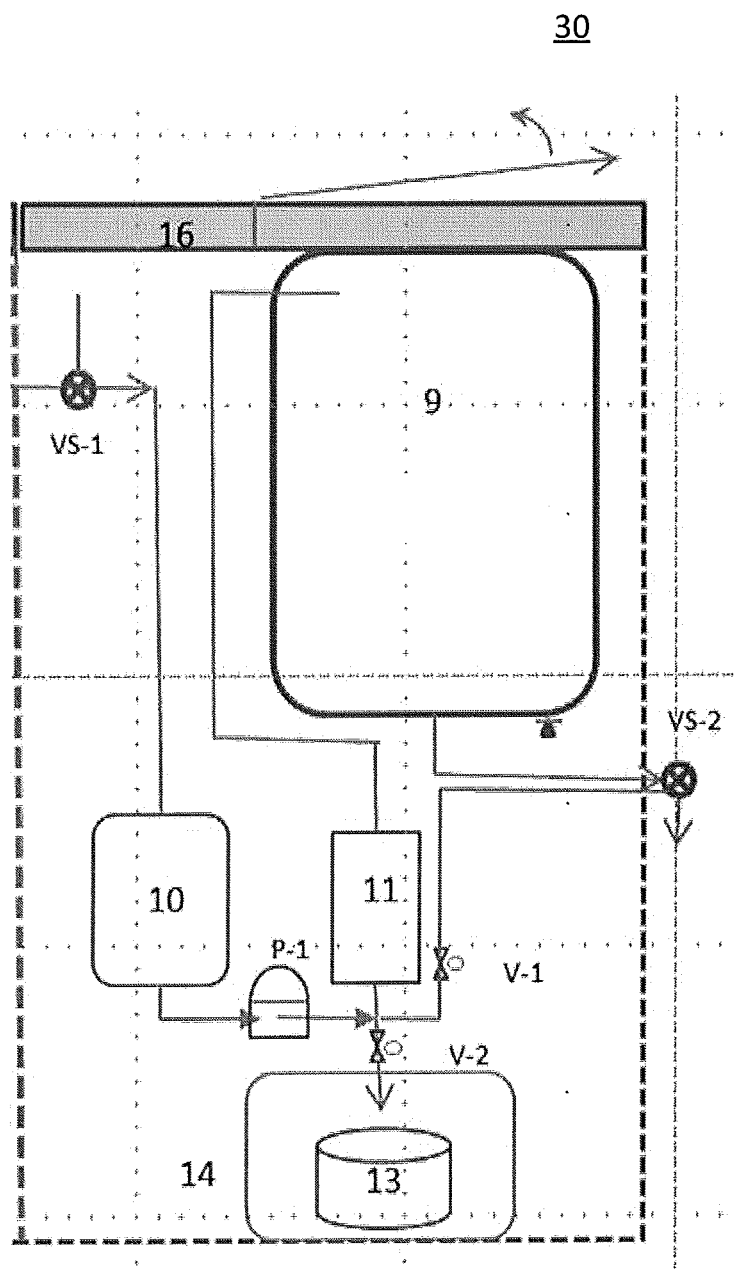
FIG. 3 illustrates an embodiment of the second compartment of FIG. 1.

Referring to FIG. 3, treated (or non-aversive containing) product such as treated Xyrem can flow into a reservoir (10) until it is full. When dispensing is desired, a metering pump (P-1) of a mixer (e.g., the mixer (D) of FIG. 1) can deliver a metered amount of the treated product from the reservoir (10) into a dilution chamber (11) as a single dose, or as a multiple of several single doses. After the dose is metered into the dilution chamber (11), a switching valve of the mixer opens up the line to a water reservoir (9), and water is gravity-fed to fill the dilution chamber (11). The dilution chamber (11) can be a fixed volume chamber (volume in a vent line of the dilution chamber can be, in some embodiments, inconsequential). With this arrangement, the volume of the diluted dose can remain substantially the same, regardless of the prescription. This can be important if a dosing cup with a fixed mark is used to verify performance of the device or to dispense from pre-diluted samples stored in a bottle (for travel purposes). However, other embodiments allow for changes in the dosage amount either manually or by link to the prescriber through internal software. Further, the dilution chamber (11) can be modified to contain variable amounts of liquid either by the use of multiple chambers, metering, or altering the volume inside the dilution chamber.

FIG. 3 illustrates a dispensing unit (30) that can include the following components, listed with exemplary, non-limiting values for sizes and volumes:

a water reservoir (9)—1-liter, fillable by user, accessed by hinged cover (16);

a treated drug product reservoir (10)—90 ml;

a diluted dose reservoir (11)—66 ml;

a product metering tube (not shown)—1 ml including volume in connections;

a diluted dose receiver ("dosing cup") (13) inserted by patient under fill nozzle during use (a balance can be used in this location to determine the weight of the cup for accurate dispensing and to see that the cup is emptied after removal);

a dispensing cavity (14), optionally with a sliding door (not shown); and enclosure and lid (16) for dispensing unit. The lid (16) can include a resealable cover, such as, for example, a lid that can be snapped in/out of place.

The device (30) can include a hinged panel for access to water reservoir (9) which detaches from lid (16) in any suitable manner, such as with a snap-and-slide mechanism. The device may also contain (e.g., as part of the mixer (D) a metering pump (P-1); a two-way pinch valve, solenoid pumps for final dilution of dose (add water to volume) (V-1) and a dispenser discharge (diluted product) (V-2); a three-way (stream select) valve solenoid actuated (VS-1) and a treatment stop, pressure vent valve (VS2). Appropriate piping is included for fluidly connecting the above components.

Drain Water Reservoir

Water is filled into a reservoir such as reservoir (9), which can be drained by a 3-way valve (VS-2). Patients may need to periodically clean the reservoir (9) and also may desire to put flavorings (like KoolAid, Crystal Light, or some other flavoring) in the water. Some additional/alternative embodiments can include: changing from gravity feed to a lift pump and either metering the water for dilution with a pump or use of an intermediate reservoir (not shown) draining back to the reservoir (9); making the water reservoir (9) removable for cleaning; use of highly reliable quick connects with check valves for disconnecting the water reservoir (9); and including water sensors in the dispensing unit (3) (e.g., in the cavity 14) to detect leaks so that the metering the dose can be precise. For example, a KNF FMM20 diaphragm pump is capable of delivering 2% RSD per stroke and would use 450 strokes per dispensing; hence, once calibrated with the treated fluid, it should be very precise. Another option is a miniature peristaltic pump, which can be of slightly larger size than the KNF FMM20.

In one embodiment of the invention, the reservoir (10) can be collapsible. When the flow from the treatment unit (e.g., the first compartment (COM1)) can't match that of the pump, the reservoir can collapse. Alternatively, the switching valve VS-1 could open to air and allow air to make up the volume—this would ensure some air in the reservoir (10), which won't be a problem unless the reservoir runs empty. If a collapsible bag is used for the reservoir (10), a level switch can be implemented to detect when there is insufficient product to dose. For example, the reservoir (10) could rest on a pressure switch sandwiched between two flat plates.

Features and Benefits

Security

In one embodiment, the dispensing device has a keyed lock that the patient can open to access the product/treatment module. In some embodiments, the only user-accessible areas of the dispensing device are for water filling (e.g., the water reservoir (9)) and receipt of dose (e.g., the reservoir (10)). The dispensing device can be assembled using secure means such as Torx security screws, to make it more difficult to open up and take from the internal reservoir(s). Other security methods to lock the dispensing device may include combination locks, electronic devices, such as card keys or wrist bracelets, and/or the like. Additionally, biometric methods such as fingerprints can be used to lock or unlock the dispensing device. More than one type of security method could be used to give an additional layer of security, such as coupling a physical control with an electronic control, or a physical control with a biometric control. Biometric controls can include a finger print, a retinal signature, a voice signature, a DNA code, a blood type, or the like, See WO2013040075 or U.S. Patent Publication No. 2013/0088328, the disclosure of each being incorporated herein by reference in the entirety.

In one embodiment where the drug is Xyrem, the entire supply for the month can housed within the dispensing device (e.g., the dispenser (DISP) or any component thereof), and the patient doesn't need to hide bottles of Xyrem. Any internally stored Xyrem that is not processed will still be protected. To access any processed, usable material in the various reservoirs of the dispensing device would require some skill and knowledge of how the machine works and misuse of Xyrem will be minimized or made more difficult.

Safety

Dosing errors can be greatly reduced or eliminated, because the dispensing device performs the dispensing and dilution. The dispensing and dilution functions can be programmed into the dispensing device. As stated above for one embodiment, there are no doses stored unsecured. The dose may be prepared in advance, but can be retained in the dispensing device until the patient is ready to take it. This protection substantially reduces the risk of misusing a prepared dose while the patient is sleeping. Also, patients having small children can protect them from accidental ingestion of the prescription drug while the patient is sleeping.

Because dosing can, in some embodiments, and to at least some extent, be governed by software, the risk of inadvertently taking more than a prescribed dose, taking an extra dose in the middle of night, or double-dosing at any time is substantially reduced. The software can control the amount of drug dispensed, the time the drug is dispensed and taken, and also dispense the drug in an accurate manner for the patient. See Ryu and Lee, J Manag Care Pharm., 2012 Jul.-Aug.; 18(6):439-45 for information on dosing errors by patients using measuring devices, the disclosure of which is incorporated herein by reference in its entirety. Additionally, the software can dilute the drug as necessary to create the required dose, such that the patient need not dispense or dilute the drug manually. In one embodiment, the software controlling the dosing is pre-programmed into the dispensing device. In an alternative embodiment, parameters of the software and/or the dispensing device can be remotely controlled or reprogrammed by a physician, enabling control and adjustment of specific doses and dilution amounts for a specific patient.

Diversion

In one embodiment, a Xyrem product has an abuse-preventing agent or additive to render it of little value for diversion purposes. Skill and patience would be required to remove any additive or aversive agents. Because the Xyrem product is in a relatively inaccessible product bag (e.g., the product bag (A), and/or the product bag (2)) and hard to pour, there is much less risk of someone stealing a bit and replacing it with water.

When an aversive is added to the Xyrem, only authorized users of Xyrem can access the dispensing device. Even if a patient willingly gives up a bottle of Xyrem, the recipient wouldn't be able to use it without the dispensing device. Software controls prevent the user from dispensing more from the dispensing device than the prescription allows. The above protections extend throughout the supply chain; when the Xyrem is denatured it is inherently less prone to diversion. Also, even without the aversive the dispensing device itself has security features that make it more difficult to divert a controlled substance, like Xyrem.

Convenience

The patient can simply press a button on the dispensing device to obtain a dose. Also, for travel, there is an option of taking pre-diluted doses as the dispensing device can dispense multiple doses (e.g., up to 5 days of dose) into bottles for travel. After dispensing travel doses, the machine can be locked out from dispensing additional doses for that period of time. Alternatively, the dispensing device can be separated into the first component (COM1) and the second component (COM2), such that the prepared product in the second component can be transported with or without the first component (COM1). The dispensing device can be sized so that travel is more convenient.

Compliance

In one embodiment, the dispensing device dispenses the prescribed dose at a given time, and when permitted by a dosing schedule. In one aspect of this embodiment, the dispensing device includes a visual and/or aural indicator, such as a light, chime, alarm, or timer, to indicate when the patient should take the prescribed dose. The indicator can facilitate administration of the drug so that the patient can see what they need to do. The indicator can go on when the dose is dispensed and off when the dosing cup is returned to the device. A weighing station (not shown) of the dispensing device can detect removal of the dosing cup and then replacement of the empty cup. See U.S. Pat. No. 5,047,948, the disclosure of which is incorporated herein by reference in its entirety. All dose preparations can be logged and recorded in the dispensing device (e.g., in a memory or database of the dispensing device) which can report to the prescriber or other monitor. It may be possible to program titration schemes for new patients, that otherwise might be difficult and confusing for the patient to implement. Additionally, the dispensing device can assist physicians in monitoring patient compliance over time. In one embodiment, the dispensing device can monitor and record the time of day each dose is taken, as well as the amount of each dose. This information can then be sent to the prescribing physician. Information entered by the patient can also be recorded and sent. In another embodiment, the dispensing device can include a digital journal where patients can enter their subjective assessments on sleep quality, mood, etc. These assessments could also be sent to the prescribing physician to provide information on efficacy of the drug in a given patient. In another aspect of the embodiment, recorded information can be sent to a patient's smartphone and/or other electronic device. In some embodiments, the dispensing device includes a docking station compatible with a smartphone or other electronic device.

Exemplary Methods

Some embodiments of the present invention include the prevention of accidental use or ingestion of the prescription drug by children, other accidental use, intentional misuse and abuse or diversion.

In some embodiments, the treatment technique can depend on the physico-chemical properties of the abuse-preventing additive and drug formulation, and can provide for selectively removing the abuse-preventing additive while leaving the drug unaffected. In particular embodiments, the technique can be complex enough that attempts by potential abusers, using readily available materials, to divert the drug for non-prescribed uses would be unsuccessful, but are reliably performed by the dispensing machine. A non-limiting list of suitable techniques include activated carbon adsorption, cation exchange resin, anion exchange resin, ion chromatography; sorption on clays, silica, or alumina, photochemical reaction (e.g., using a UV lamp), filtration, ultrafiltration, and osmosis.

In other embodiments, the treatment technique may also involve chemical conversion of the drug or additive. For example, cleavage of the abuse-preventing additive may render it inactive, palatable, non-odorous, or non-colored.

In many embodiments, the formulation of the present invention is subsequently diluted prior to administration to the patient. In some embodiments, the dilution may precede treatment. In other embodiments, the dilution medium may flow through one or more of the treatment modules (such as beds, filters, or filter cartridges) after the formulation is treated in order to more effectively recover beneficial agents.

One skilled in the art will appreciate that the separation technique will depend on differences in molecular size, lipophilicity, isoelectric point or pKa, and possibly structural moieties between the drug and additive or denaturant. In general, carbon filtration is useful if the drug does not bind appreciably to carbon yet the abuse-preventing additive does. Cation or Anion exchange beads, columns, or resins are useful when the denaturant is ionized but the drug is not, or when the pKa difference between drug and abuse-preventing additive is large. Bed chromatography is useful when the pKa difference is smaller. When the drug is ionized and water-soluble, yet the denaturant is not, carbon filtration is often a suitable method. Osmosis or ultrafiltration can potentially be useful if the drug molecule is relatively small and the abuse-preventing additive molecule is relatively large in size. UV treatment can be useful if the abuse-preventing additive undergoes photolytic reaction but the drug does not, provided the formulation absent abuse-preventing additives does not substantially absorb radiation at the selected UV wavelength. Filtration is useful when the abuse-preventing additives are presented as a fine suspension, but the drug is in solution. It can also be useful when the drug is presented as a suspension and the abuse-preventing additives are in solution.

The means of removing the abuse-preventing additive need not be completely selective to the additive. Thus, a removal technique that removes substantially more abuse-preventing additive than beneficial active agent may be useful and effective. For example, the tendency and extent to which compounds adsorb onto activated carbon varies widely depending on the properties of the compound. As a predominantly equilibrium process, all that may be required is that the carbon bed, when equilibrated with the desired drug at its concentration in the formulation medium, has capacity to further adsorb the abuse-preventing additive it is intended to remove. In cases where the adsorption medium, such as carbon, also binds to the active agent, adsorption of the additive may occur by displacing the active agent or using additional sorption sites not accessible to the active agent.

In other cases, relative removal is more important than absolute removal. For example, Xyrem® has a concentration of about 42 wt % sodium oxybate in solution whereas denatonium at a concentration of 50 ppm (or 0.005%) is a very effective aversive. Although a small fraction of sodium oxybate may bind to the carbon, it is of no practical consequence as long as most of the denatonium is also removed. In cases where the active agent and additives (aversive or otherwise) are employed in comparable amounts, the selectivity of removal becomes a much more important factor in selection of technique.

In some embodiments where sorption media, such as activated carbon, are employed to remove the additive, the dispenser can provide the treated product as a suspension with the media present. Activated carbon, for example, effectively removes many aversives and would render the formulation palatable without requiring removal of the carbon. In some embodiments where the abuse-preventing additive is an agent producing an undesirable physiological effect, removal of the carbon may not be needed as long as the agent remains bound to the carbon as it travels through the GI tract as would be expected for many highly lipophilic agents.

In one embodiment of the invention, a dilution step occurs after treatment to remove the abuse-preventing additive(s). It is conceivable that the treatment method may also remove functional additives, such as flavors, sweeteners, or other ingredients. In such cases, these ingredients may be returned to the formulation in the dilution step. The dilution medium is normally aqueous, but can also be a complex vehicle containing solvents, solubilizers, viscosifiers, colorants, flavors, and sweeteners for example.

In another embodiment, the invention includes a GHB composition that has been processed by a device to have substantially all of the abuse-preventing additive removed, altered or changed so that the composition is effective when administered to the patient and is also safe for human consumption and palatable. In another embodiment, the invention includes a GHB-containing dosage form, including a liquid dosage form, that has been processed by a device to have substantially all of the abuse-preventing additive removed, altered or changes to that the composition is effective when administered to the patient and is also safe for human consumption and palatable. In another embodiment, the processed GHB dosage form comprises a pharmaceutically acceptable carrier, the formulation containing GHB at a concentration of between 350 and 750 mg/mL and a pH between 6.5 and 10.

Many drug products contain two beneficial pharmaceutical agents, where one is prone to abuse and the other is not. Examples of such combination products include hydrocodone bitartrate/acetaminophen (Vicodin) and tramadol/acetaminophen (Ultracet). In some embodiments, it may be useful to provide the second beneficial agent, which is not prone to abuse, in the dilution medium or to otherwise add it to the formulation as part of the dispenser operation after the treatment step to remove the aversive agents or additives. It can be presented in the dilution medium, for example, as a solution or a suspension, and in an appropriate concentration so that the dilution volume provides the desired dose.

Many drug products offer features of delayed, sustained, or patterned release that can be achieved by coating beads containing a controlled substance with a rate-controlling polymer for sustained release and/or one or more pH-sensitive polymers for delayed release either in small intestine or large intestine. In one embodiment of the invention, a modified release bead containing a controlled substance is further coated with an aversive or antagonistic agent rendering the product undesirable. In the dispenser provided for legitimate use, the abuse-preventing agent is removed by dissolving the outer coating containing the abuse-preventing agent without substantially affecting the controlled release coating that governs release of the beneficial but abusable agent. The intact modified release beads are retained in a filter, whereas the abuse-preventing agent is rinsed to a waste reservoir by the machine. Next, the beads are dispensed by back-washing the filter and conveying the suspended beads to a dosing cup for the patient.

In some embodiments of the invention, the treated formulation—absent the abuse-preventing additives to deter abuse—is retained on a filter. The filter cake is then dispensed to a capsule by resuspension in a medium compatible with capsules (such as some medium or long-chain triglycerides, solubilizing agents, and cosolvents such as ethanol, propylene glycol, or polyethylene glycol). Other means of conveying the filter cake to a discrete dosage form may be contemplated, with varying degrees of complexity.

In one embodiment of the invention, the abuse-preventing additive can have a chemical group which can facilitate removal. Such separation methods are known in the art and include affinity chromatography for example. A bispecific ligand can be attached to a molecule which can be removed with a matrix such as agarose, cellulose, sepharose, or toyopearl beads, tubes or other shapes. Equipment for this separation can be found at commercial supply houses such as Sigma Aldrich and others.

In another embodiment of the invention, chemical oxidation can be a useful means of removing the abuse-preventing additive, provided the abuse-preventing agent is sensitive to oxidation and the target drug—such as sodium oxybate—is not prone to such oxidation. In such cases, it may be necessary to remove the excess oxidizer, for example by adding sodium metabisulfite, sodium sulfite, ascorbic acid, or a similar mild reducing agent after the aversive is sufficiently oxidized. Other means of oxidation, provided the drug is not destroyed in the process, include use of hydrogen peroxide and also Fenton chemistry where ferrous sulfate is added to catalyze the formation of hydroxyl radicals.

In another embodiment, the common ion effect may be used as a means to separate the abuse-preventing agent from the drug by addition of a salt having the same counterion as either the drug or the aversive or antagonistic additive. For example, one may be able to selectively precipitate naltrexone HCl from a solution containing it and morphine sulfate by, for example, simply adding about 50-300 mg/mL sodium chloride. The morphine sulfate remaining in solution with sodium chloride would be removed from the naltrexone HCl precipitate by filtration. In similar fashion, an aversive or antagonist may be removed by precipitating the active species using the common ion effect, capturing the precipitated active by filtration, and then back-washing the filter cake with water and flowing into a dispensing cup for administration to the patient.

In another embodiment, the abuse-preventing additive and active drug may be present both as particles in suspension. Such particles may be separable by applied magnetism, provided the aversive particle comprises a ferromagnetic seed. Such particles may be prepared, for example, by fluid bed granulation techniques where the abuse-preventing agent and other additives (such as film-forming polymer and filler) is sprayed in solution onto 100 mesh iron powder. The resulting aversive particles are then added to a suspension of the drug particles. Upon dispensing, the combined suspension flows through a channel having a strong magnetic field applied to its surface. The active particles flow through the chamber, while the aversive particles are trapped on its surface. After dispensing, the magnetic field is removed and the aversive particles are rinsed to a waste collection vessel.

It may be useful to have a dye as an indicator in addition to any other additives or denaturants to show when the GHB has been processed and is safe to ingest. When the medication is clear or non-colored, the medication is ready for use as the user will know that any and all other abuse-preventing agents have been removed, converted, or otherwise neutralized.

In another embodiment of the invention, the drug itself is rendered inactive by attaching moieties that either prevent absorption or interfere with its activity. The drug is then activated in the dispensing device by a chemical reaction. Means of preventing absorption include attachment of groups that change solubility, such as lipophilic groups that reduce water solubility or attachment of hydrophilic groups that reduce the drug's lipophilicity substantially. Alternatively, structural groups can be included that interfere with active transport. Activity can be negated by adding structural groups such that the drug does not effectively bind to the target receptor. Reversible chemical modification is practiced in pro-drug design (such as esterification of carboxylic acids or acylation of alcohol groups—either of which hydrolyze in-vivo to the desired drug), but extemporaneous use of it as a means to prevent diversion or misuse has heretofore not been suggested.

In another embodiment, two methods or features may be used to control access to the prescription medication. In one embodiment, the medication can be modified or an abuse-preventing additive can be provided to the formulation. For example, a pro-drug of the target drug can be provided as the concentrated solution to the patient, one embodiment is GBL. One or more of the abuse-preventing additives are provided to the solution prior to distribution to the patient, and the dispensing device both removes the undesirable abuse-preventing additives and also converts the pro-drug into the target compound. This embodiment may be particularly useful for drugs that are carboxylic acid salts that are relatively insoluble in organic solvents. In that event, the drug can be provided as an ester prodrug. For example, gamma butyrolactone (GBL) is the precursor to GHB (also known as oxybate) and is an excellent solvent for many potential additives, yet the salt forms of oxybate are insoluble in most organic solutions. Therefore, oxybate salt formulations are limited to aqueous solutions that may have limited ability to solvate many additives. As an example of this embodiment, GBL can carry a lipophilic additive rendering the mixture undesirable and then, in the dispensing device, be converted to an oxybate salt having poor carbon absorption without affecting the additive. The resulting mixture can be passed through a bed of activated carbon to remove the additive. Alternatively, because GBL also has relatively poor loading on carbon, it can also be passed through the carbon bed unchanged and subsequently converted to its oxybate or left unchanged, if GBL is instead the intended therapeutic agent.

In yet another embodiment of the invention, the original product is a powder intended to be diluted to a solution or suspension by the patient or caregiver. An example of such a product is Quillivant XR (methylphenidate extended release powder for suspension). In this instance, admixing of one or more of the aforementioned additives would render the powder unsuitable for use unless processed through the dispensing device.

In another embodiment, the product is provided as a solid dosage form such as a tablet or capsule that optionally contains one of more of the aforementioned abuse-preventing additives rendering it unsuitable for use. The patient drops the tablet into the dispensing machine, and the machine dissolves the tablet, optionally crushing it first to aid the dissolution, and then removes the objectionable abuse-preventing additive(s), and dispenses a solution ready for ingestion as prescribed. Some abuse-preventing additives may not be preferred for tablets or capsules, as swallowing these dosages forms may largely bypass taste and smell. Other types of abuse-preventing additives, such as those producing counter-effect or undesirable physiological effect, may be more useful. Some additives, such as capsaicin, though primarily useful for pungency may be useful for the unpleasant irritation it can produce in the GI tract.

The abuse-preventing additive(s) (e.g., aversive agents or denaturant(s)) may be added individually or as a mixture to the pharmaceutical composition anywhere between and including the manufacturing facility and the pharmacy. The present invention is also directed to products made by such methods of preparation.

Pharmaceutical compositions comprising the abuse-preventing additive(s) and the medication (optionally with other medicines) may be prepared according to conventional pharmaceutical compounding techniques. The compositions may take a wide variety of forms depending on the form of preparation desired for administration, e.g., intravenous, oral or parenteral. The compositions according to this invention may, for example, take the form of liquid preparations for oral administration, such as solutions and non-aqueous suspensions. The formulation can also be in the form of a solid, such as tablets, capsules, granules, powders, or lozenges.

The compositions may be formulated using conventional carriers or excipients and well established techniques. Without being limited thereto, such conventional carriers or excipients include diluents, binders and adhesives (e.g., cellulose derivatives and acrylic derivatives), lubricants (e.g., magnesium or calcium stearate, or vegetable oils, polyethylene glycols, talc, sodium lauryl sulphate, polyoxyl ethylene monostearate), disintegrants, colorants, flavorings, preservatives, sweeteners and miscellaneous materials such as buffers and adsorbents (some of which would be considered denaturants) in order to prepare a particular composition. See U.S. patent application Ser. No. 13/071,369, and U.S. Pat. Nos. 8,771,735 and 8,778,398.

Non-aqueous suspensions may be obtained by dispersing the abuse-preventing additive and medication compositions in a suitable non-aqueous based vehicle, optionally with the addition of suitable viscosity enhancing agent(s) (e.g., hydrogenated edible fats, aluminum stearate, etc.). Suitable non-aqueous vehicles include, for example, almond oil, *arachis* oil, soybean oil or fractionated vegetable oils such as fractionated coconut oil, propylene glycol, PEG 400, glycerol, ethanol, diethylene glycol monoethyl ether (Transcutol), glycofurol, macrogol 15 hydroxystearate (Solutol), polyoxyl35 castor oil (Cremophor EL). Preservative(s) (e.g., methyl, ethyl, propyl or butyl-hydroxybenzoates, sodium benzoate or sorbic acid, etc.) may be included as appropriate.

REMS Type System

As stated above, one embodiment of the present invention is a method and a device, such as the dispensing device (DISP) of FIG. 1, to control access to, monitor use, prevent abuse, unauthorized use, or misuse of a prescription drug which may be a controlled substance. It can be a system of two or more parts. In the simplest form, it does not employ an abuse-preventing additive, but relies on the above described features of the device to ensure safety, compliance, controlled use, and convenience. In another embodiment, it is a two part system in which one part resides in the drug and the other in the device. Both parts are needed to enable a patient to ultimately safely use the drug. The part that resides in the drug includes those items listed above which include additives, denaturants, colorants, chemical conversions, and the like. The device is the component that can render the drug safe or otherwise ingestible.

The drugs can be subject to the controls that are known in the industry to further enhance the ability to prevent abuse and misuse. A REMs system as defined in the above patents, including U.S. Pat. Nos. 7,765,106; 7,765,107; 7,668,730; 7,797,171; 7,895,059; and 8,457,988, can be implemented to provide security for drug distribution. The same system can be employed for distributing the device to further ensure the safety of the whole process. For example, the drug can be distributed by a central pharmacy using a centralized database of users and prescribers as in the above patents. Also, multiple pharmacies and databases can be used if there is sufficient and adequate communication among the entities in the transport and supply chain.

In addition, to prevent unauthorized access to the device by theft or otherwise, the device may need to be activated for use by an authorized person, such as the pharmacy, which could be one central pharmacy with a central database of the devices, or a network of pharmacies and databases that are connected together to ensure proper communication regarding authorized use of the drug and device.

Use of the device can be authorized and controlled by an authorized person or agent through the appropriate software components, whether it is one central control center, pharmacy, or through a central database. The software can lock out and prevent access to treated drug, such as Xyrem. It can prevent dosing, processing, and further use. Authorization can be effected over the internet using the typical internet connections for communication. The communication can be subject to security precautions for access to sensitive sites. The device can record and report on usage so that the authorizing agent can determine the volume of use, for example, as one indicator or abuse or misuse. If misuse or abuse is indicated, then permission is revoked and the patient would need to physically return to the authorizing agent, pharmacy, etc. for redetermination of authorized use and reauthorization. Authorization can be accomplished through, for example, encryption or similar security technology. An authorized user can use a password or other identification measures, either singly or in combination, to use the device. A multi-part system in which more requirements are presented as gating items to deter abuse or misuse is more effective. One embodiment of the system employs 2, 3, 4, 5, 6, or more features that present an impediment for an unauthorized user, but not for an authorized user.

EXAMPLES

The following examples are not meant to be limiting, but serve to demonstrate the range of applications possible with this method of conveying abuse deterrence on liquid formulations.

Example 1

Xyrem® is a 500 mg/mL solution of sodium oxybate in water that is pH-adjusted with malic acid. Denatonium benzoate is added at about 50 ppm, rendering the product undrinkable. The product is bottled and distributed through a central pharmacy to the patient. The patient places the bottle in a custom-designed dispenser. When a dose is requested and permitted (by programming of the device), about 6-9 mL of the Xyrem® liquid is pumped to a packed bed of about 1-10 mL fine activated carbon. About 60 mL of tap water is then pumped through the same packed bed, flushing the remaining sodium oxybate and malic acid into a dosing cup while the bed retains the denatonium. The diluted product retains a high degree or all of its potency, and denatonium is substantially removed so that it is rendered palatable for administration.

Example 2

Capsaicin is added to Xyrem® at a level of about 10 ppm. Methylene blue is added a level of about 100 ppm. The formulation has a blue color and is extremely pungent to taste. The product is bottled and distributed to the patient. Placed in a dispensing device, about 6-9 mL of the solution is passed through a bed of fine activated carbon, and rinsed with about 60 mL of tap water into a dosing cup. The diluted product has no color and retains a high degree of its potency, has no capsaicin, and is palatable to drink.

Example 3

In this example, an active prodrug of GHB having better solubility for a denaturant (capsaicin) is employed. An approximately 4-molar solution of gamma butyrolactone (GBL) is first prepared. To this is added about 100 ppm capsaicin. The solution is packaged and distributed to the patient. The dispensing device has, as its separation module, two beds in series—the first bed is calcium hydroxide, and the second bed is activated carbon. About 6-9 mL of the concentrated GBL is pumped slowly to the beds, such that the GBL is reacted with calcium hydroxide in sufficient time. Next, about 60 mL of tap water for dilution is flowed through the two beds to rinse the calcium oxybate into the dosing cup. The capsaicin is effectively removed by the carbon bed.

Example 4

An opioid/antagonist combination is compounded as a fine suspension of micronized naltrexone anhydrous free base, 1 mg/mL in a solution of 20 mg/mL morphine sulfate and 0.1% xanthan gum (as thickener) in water. A blue dye is added at 100 ppm. The product is bottled and distributed to the patient. The product is placed in a dispensing device by the patient, on demand, and per prescribed programming 0.5-5 mL of the concentrate is passed through a 0.5-micron filter into a dosing cup. About 30-60 mL of water is then flushed through the filter into the dosing cup to recover the entire dose of morphine sulfate absent any naltrexone particles. The color intensity of the diluted solution is an indication of the strength.

Example 5

A solution containing a mixture of four salts of oxybate (sodium, calcium, magnesium, and potassium) is compounded to a 4M concentration of oxybate. To this is added 200 ppm Gentian violet, a gram-negative stain. The blue solution is packaged and distributed to the patient. In normal use, the patient uses the automatic dispenser to dispense 6 mL of concentrate through a carbon bed, rinsed with about 60 mL of tap water to recover all of the drug and none of the Gentian violet. The solution ready for administration is clear. Any misuse will show the dye in the mouth or on the gums, lips and tongue of the (mis)user.

Example 6

A largely inactive proform of GHB, in the form of an n-polyol (C4 or greater) ester of GHB, is provided as an approximately 4M aqueous solution. This composition is expected to be largely unabsorbed throughout the GI tract. The solution is bottled and distributed to the patient. In use, the patient places it in the dispenser, whereupon the dispenser pumps the entire bottle through a bed of calcium hydroxide, optionally at an elevated temperature, at a rate slow enough to ensure complete conversion of the inactive proform into calcium oxybate and the polyol. The calcium oxybate/polyol solution is then stored in an internal reservoir and, as prescribed and on demand, diluted and dispensed to the patient by the device.

Example 7

An approximately 4M aqueous solution of GBL containing about 50 mg/mL niacin and spearmint flavoring is bottled and distributed to the patient. The bottle is loaded into the dispensing device, along with a resin cartridge delivered to the patient separately. In each dispensing, about 6-9 mL of concentrated solution is passed onto the resin cartridge, and then about 60 ml of tap water diluent is pumped by the device through the same cartridge and into the dosing cup. A single dose of diluted product free of niacin is therefore provided.

Example 8

The system of Example 7 is employed, except the solution after passing through the resin cartridge is then passed through a bed of calcium hydroxide, thus converting the GBL into calcium oxybate.

Example 9

A small amount of capsaicin was extracted from 2 large jalapeno peppers in 100 mL water by blending the peppers to a pulp and then filtering. The resulting chili water was divided in two portions. One portion was treated with 0.2% activated carbon (pharmaceutical grade powder) for about 15 minutes, and the other portion was retained as a reference. This treatment completely removed the taste of the capsaicin, according to two tasters. Although the initial capsaicin concentration was not determined in this test, it does confirm that the capsaicin is removed substantially below the threshold of taste. Hence, carbon filtration is an effective way to remove capsaicin.

Example 10

In a lab evaluation, 60 ppm sucrose octaacetate in water was evaluated. (This is the level appropriate in diluted product if 600 ppm of Xyrem® is used.) It is intensely bitter. Upon treatment with about 50 mg/L lime at room temperature for 10 minutes, the product had no taste whatsoever. Hydrolysis products are sucrose and calcium acetate.

Example 11

In a lab evaluation, 90 ppm denatonium saccharide in water was prepared. To 40 mL samples were added 100 mg and 100 0 mg, respectively, of powdered activated carbon Ecosorb EC-947. The samples were stirred for about 2 days to equilibrate. After removal of the carbon by centrifuge, about 1-2 mL of each sample was tasted and swallowed and found to be virtually indistinguishable from water. In comparison, the untreated sample was intensely bitter, as about 0.1 mL placed on the tongue could be tasted for at least two hours after administration.

Example 12

During manufacturing, 90 ppm denatonium benzoate is added to Xyrem®, rendering it abuse-resistant. The Xyrem® is bottled and sent to a central pharmacy. A patient is prescribed Xyrem®, and the prescription is sent to a central pharmacy for fulfillment. The central pharmacy optionally sends the patient instructions and a dispensing machine, similar to that described in FIG. 1-3. The machine is programmed either at the factory or by the pharmacist to reflect the prescribed dosing. Upon confirmation of receipt of the dispensing machine, the central pharmacy sends the patient the Xyrem®. The patient loads the bag of Xyrem® into the machine, following instructions provided, turns the machine on and verifies the dosage settings. During the day, and perhaps for more than one day, the machine continuously treats the Xyrem® at a slow rate until there is sufficient capacity of treated material for dispensing. After that point, the patient—immediately prior to sleeping—requests a first dose and the dispenser provides it. The machine provides a second dose 2-4 hours after the first dose. The dispenser will not provide any further doses until at least 12 h have passed. After about a month of taking the medication, the dispenser indicates that the product bag is empty. The machine continues to dispense up to 5 more days supply and, in the interim, the patient secures and installs the next months' supply of Xyrem® provided by a central pharmacy. After about a year of using the dispenser, an indicator (or a phone call from a pharmacy or supplier agent) reminds the patient to service the treatment module. The patient disconnects the treatment module, sends it to a pharmacy or service location, and receives within 4 days either the serviced module or a replacement module. The patient separately receives the resupply of Xyrem®. In the interim, the dispenser continues to dispense up to 5 days from an internal reservoir of treated product.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible.

The functions of any element may be carried out in various ways in alternative embodiments. All cited references, patent and/or patent applications are herein incorporated by reference in their entirety for all purposes.

The invention claimed is:

1. A method, comprising:
loading a device with a substance, wherein loading is performed by a user of the substance;
receiving a dosing schedule, the dosing schedule including an indication of a dose amount of the substance and a set of dosing times;
communicating, at a first dosing time of the set of dosing times, an indication to the user of the device, availability of the substance, the device including a compartment configured to hold the substance, a diluent reservoir configured to hold a diluent, and a dilution chamber configured to hold a diluted form of the substance;
diluting the substance by pumping the substance into the dilution chamber and adding the diluent to the dilution chamber;
receiving a first request from the user to dispense the substance;
operating a valve of the device for dispensing the dose amount of the substance at the first dosing time;
communicating, to the user, an indication of a lockout period during which dispensing of the substance is prohibited;
communicating, at a second dosing time of the set of dosing times, the indication to the user of availability of the substance and of expiration of the lockout period;
receiving a second request from the user to dispense the substance; and
operating the valve for dispensing the dose amount of the substance at the second dosing time.

2. The method of claim 1, wherein the substance includes gamma hydroxybutyrate (GHB), a salt, a precursor, or a prodrug thereof.

3. The method of claim 1, wherein the compartment is removable, further comprising coupling the compartment to a chamber of the device.

4. The method of claim 1, wherein the dosing schedule is a first dosing schedule and the dose amount is a first dose amount, further comprising:
receiving the first dosing schedule, the first dosing schedule including an indication of a first dose amount of the substance and the first dosing time;
communicating, at the first dosing time, the indication to the user of availability of the substance;
receiving the first request from the user to dispense the substance;
operating the valve for dispensing the first dose amount of the substance at the first dosing time;
communicating, to the user, an indication of the lockout period during which dispensing of the substance is prohibited;
receiving a second dosing schedule, the second dosing schedule including an indication of a second dose amount of the substance and the second dosing time, the second dose amount different from the first dose amount;
communicating, at the second dosing time, the indication to the user of availability of the substance and of expiration of the lockout period;
receiving the second request from the user to dispense the substance; and
operating the valve for dispensing the second dose amount of the substance at the second dosing time.

5. The method of claim 1, further comprising:
receiving an indication to dispense multiple dose amounts of the substance at a third dosing time;
operating the valve for dispensing the multiple dose amounts of the substance at the third dosing time; and
communicating, to the user, an indication of an extended lockout period during which dispensing of the substance is prohibited, the extended lockout period based on a sum of multiple lockout durations, each lockout duration associated with a dose amount of the multiple dose amounts.

6. The method of claim 1, further comprising:
generating compliance information association with dispensing of the substance at the first dosing time, at the second dosing time, or both; and
transmitting an indication of the compliance information.

7. The method of claim 2, the transmitting the indication of the compliance information including transmitting the indication of the compliance information to a risk evaluation and mitigation strategy (REMS) system.

8. The method of claim 1, further comprising:
generating compliance information association with dispensing of the substance at the first dosing time, at the second dosing time, or both; and
storing an indication of the compliance information to a memory of the device.

9. The method of claim 1, the communicating the indication of the lockout period including communicating the indication of the lockout period to a light indicator of the device.

10. The method of claim 1, further comprising generating the diluted form of the substance by:
pumping a metered amount of an undiluted form of the substance from the first compartment into the dilution chamber; and
delivering a diluent from the diluent reservoir to the dilution chamber.

11. The method of claim 10, wherein delivering comprises gravity-driven delivery of the diluent from the diluent reservoir to the dilution chamber.

12. The method of claim 10, wherein the diluent is water.

13. The method of claim 1, wherein the valve is coupled to a controller, and wherein the controller automates operation of the valve to dispense the dose amount of the substance at the first dosing time or the second dosing time, or at both times.

14. The method of claim 1, wherein operating the valve of the device is controlled by the user.

15. A method for delivering a substance to a user using a dispensing device comprising:
loading the dispensing device with the substance, wherein loading is performed by the user;
programming the dispensing device with a dosing schedule, the dosing schedule including an indication of a dose amount of the substance and a set of dosing times;
receiving a request from the user to dispense the substance;
delivering the dose amount of the substance into a dilution chamber using a metering pump;
diluting the substance by adding a diluent to the dilution chamber; and
dispensing the diluted substance according to the dosing schedule.

16. The method of claim 15, wherein the substance includes gamma hydroxybutyrate (GHB), a salt, a precursor, or a prodrug thereof.

17. The method of claim 15, wherein dispensing the diluted substance is controlled by the user.

18. A method for delivering one or more doses of a substance to a user comprising:
   loading a dispensing device with the substance, wherein loading is performed by the user,
   programming the dispensing device with a dosing schedule, the dosing schedule including an indication of a dose amount of the substance and a set of dosing times;
   diluting the substance in the dilution chamber of the dispensing device, wherein diluting comprises delivering the dose amount of the substance into the dilution chamber using a metering pump and adding a diluent to the dilution chamber; and
   delivering the diluted substance according to the dosing schedule, wherein the user operates the device to deliver the one or more doses.

19. The method of claim 18, wherein the substance includes gamma hydroxybutyrate (GHB), a salt, a precursor, or a prodrug thereof.

\* \* \* \* \*